US008563246B2

(12) United States Patent
Chee et al.

(10) Patent No.: US 8,563,246 B2
(45) Date of Patent: *Oct. 22, 2013

(54) COMBINATORIAL DECODING OF RANDOM NUCLEIC ACID ARRAYS

(75) Inventors: Mark S. Chee, Encinitas, CA (US); David R. Walt, Lexington, MA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/532,606

(22) Filed: Jun. 25, 2012

(65) Prior Publication Data
US 2012/0264622 A1    Oct. 18, 2012

Related U.S. Application Data

(60) Continuation of application No. 13/159,302, filed on Jun. 13, 2011, now Pat. No. 8,206,917, which is a continuation of application No. 12/506,116, filed on Jul. 20, 2009, now Pat. No. 7,960,119, which is a continuation of application No. 11/625,708, filed on Jan. 22, 2007, now Pat. No. 7,563,576, which is a continuation of application No. 10/648,848, filed on Aug. 21, 2003, now Pat. No. 7,166,431, which is a division of application No. 09/574,117, filed on May 19, 2000, now Pat. No. 6,620,584.

(60) Provisional application No. 60/135,052, filed on May 20, 1999.

(51) Int. Cl.
*C12Q 1/68* (2006.01)

(52) U.S. Cl.
USPC .......................................... 435/6.1; 435/6.11

(58) Field of Classification Search
None
See application file for complete search history.

(56) References Cited

U.S. PATENT DOCUMENTS

| | | | |
|---|---|---|---|
| 4,200,110 A | 4/1980 | Peterson et al. |
| 4,499,052 A | 2/1985 | Fulwyler |
| 4,682,895 A | 7/1987 | Costello |
| 4,785,814 A | 11/1988 | Kane |
| 4,811,218 A | 3/1989 | Hunkapiller et al. |
| 4,822,746 A | 4/1989 | Walt |
| 4,824,789 A | 4/1989 | Yafuso et al. |
| 4,883,750 A | 11/1989 | Whiteley et al. |
| 4,988,617 A | 1/1991 | Landegren et al. |
| 4,999,306 A | 3/1991 | Yafuso et al. |
| 5,002,867 A | 3/1991 | Macevicz |
| 5,028,545 A | 7/1991 | Soini |
| 5,105,305 A | 4/1992 | Betzig et al. |
| 5,114,864 A | 5/1992 | Walt |
| 5,132,242 A | 7/1992 | Cheung |
| 5,143,853 A | 9/1992 | Walt |
| 5,194,300 A | 3/1993 | Cheung |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,302,509 A | 4/1994 | Cheeseman |
| 5,320,814 A | 6/1994 | Walt et al. |
| 5,357,590 A | 10/1994 | Auracher |
| 5,380,489 A | 1/1995 | Sutton et al. |
| 5,403,708 A | 4/1995 | Brennan et al. |
| 5,407,798 A | 4/1995 | Martinelli et al. |
| 5,435,724 A | 7/1995 | Goodman et al. |
| 5,474,895 A | 12/1995 | Ishii et al. |
| 5,481,629 A | 1/1996 | Tabuchi |
| 5,494,798 A | 2/1996 | Gerdt et al. |
| 5,494,810 A | 2/1996 | Barany et al. |
| 5,496,997 A | 3/1996 | Pope |
| 5,503,980 A | 4/1996 | Cantor |
| 5,512,490 A | 4/1996 | Walt et al. |
| 5,516,635 A | 5/1996 | Ekins et al. |
| 5,518,883 A | 5/1996 | Soini |
| 5,552,278 A | 9/1996 | Brenner |
| 5,565,324 A | 10/1996 | Still et al. |
| 5,573,909 A | 11/1996 | Singer et al. |
| 5,575,849 A | 11/1996 | Honda et al. |
| 5,604,097 A | 2/1997 | Brenner |
| 5,633,972 A | 5/1997 | Walt et al. |
| 5,639,603 A | 6/1997 | Dower et al. |
| 5,656,241 A | 8/1997 | Seifert et al. |
| 5,679,524 A | 10/1997 | Nikiforov et al. |
| 5,690,894 A | 11/1997 | Pinkel et al. |
| 5,700,637 A | 12/1997 | Southern |
| 5,750,341 A | 5/1998 | Macevicz |
| 5,763,175 A | 6/1998 | Brenner |

(Continued)

FOREIGN PATENT DOCUMENTS

CA    2130562       9/1993
EP    0 269 764 B1  8/1988

(Continued)

OTHER PUBLICATIONS

Abel, A.P., et al., "Fiber-optic evanescent wave biosensor for the detection of oligonucleotides," *Anal. Chem.* 68(17):2905-2912 (Sep. 1996).

Angel, S.M., "Optrodes: Chemically Selective Fiber-Optic Sensors," *Spectroscopy* 2(4):38-47 (1987).

Anon., "Fluorescent Micorspheres," *Tech. Note 19*, Bangs Laboratories: Fishers, IN (Feb. 1997).

Anon., "Molecular Luminescence Spectroscopy Methods and Applications, Part I," *Chemical Analysis*, vol. 77, Schulman (ed.), Wiley & Sons, Inc.: New York, NY (1985).

(Continued)

*Primary Examiner* — Young J Kim
(74) *Attorney, Agent, or Firm* — Knobbe, Martens, Olson & Bear, LLP

(57) ABSTRACT

Methods disclosed herein relate to identification of nucleotides in a nucleotide sequence.

20 Claims, 6 Drawing Sheets

(56) References Cited

U.S. PATENT DOCUMENTS

| | | | |
|---|---|---|---|
| 5,780,231 A | 7/1998 | Brenner | |
| 5,795,714 A | 8/1998 | Cantor et al. | |
| 5,798,210 A | 8/1998 | Canard et al. | |
| 5,800,994 A | 9/1998 | Martinelli et al. | |
| 5,814,524 A | 9/1998 | Walt | |
| 5,830,711 A | 11/1998 | Barany et al. | |
| 5,840,256 A | 11/1998 | Demers et al. | |
| 5,854,684 A | 12/1998 | Stabile et al. | |
| 5,856,083 A | 1/1999 | Cheisky et al. | |
| 5,858,732 A | 1/1999 | Solomon et al. | |
| 5,863,708 A | 1/1999 | Zanzucchi et al. | |
| 5,876,924 A | 3/1999 | Zhang et al. | |
| 5,877,280 A | 3/1999 | Wetmur | |
| 5,888,723 A | 3/1999 | Sutton et al. | |
| 5,900,481 A | 5/1999 | Lough et al. | |
| 5,962,225 A * | 10/1999 | Ramberg | 435/6.16 |
| 5,969,119 A | 10/1999 | Macevicz | |
| 5,972,619 A | 10/1999 | Drmanac et al. | |
| 6,007,987 A | 12/1999 | Cantor et al. | |
| 6,013,456 A | 1/2000 | Akhavan-Tafti | |
| 6,023,540 A | 2/2000 | Walt et al. | |
| 6,027,889 A | 2/2000 | Barany et al. | |
| 6,051,380 A | 4/2000 | Sosnowski et al. | |
| 6,054,564 A | 4/2000 | Barany et al. | |
| 6,083,763 A | 7/2000 | Balch | |
| 6,110,678 A | 8/2000 | Weisburg et al. | |
| 6,172,218 B1 | 1/2001 | Brenner | |
| 6,251,639 B1 | 6/2001 | Kurn | |
| 6,266,459 B1 | 7/2001 | Walt et al. | |
| 6,268,148 B1 | 7/2001 | Barany et al. | |
| 6,306,597 B1 | 10/2001 | Macevicz | |
| 6,327,410 B1 | 12/2001 | Walt | |
| 6,498,013 B1 | 12/2002 | Velculescu et al. | |
| 6,620,584 B1 | 9/2003 | Chee et al. | |
| 6,620,594 B1 | 9/2003 | Giacobino et al. | |
| 6,746,845 B2 | 6/2004 | Kinzler et al. | |
| 6,855,523 B2 | 2/2005 | Zhang et al. | |
| 7,070,927 B2 | 7/2006 | Drmanac | |
| 7,166,431 B2 | 1/2007 | Chee et al. | |
| 7,563,576 B2 | 7/2009 | Chee et al. | |
| 7,960,119 B2 | 6/2011 | Chee et al. | |
| 8,206,917 B2 * | 6/2012 | Chee et al. | 435/6.1 |

FOREIGN PATENT DOCUMENTS

| | | |
|---|---|---|
| EP | 0 372 524 A2 | 6/1990 |
| EP | 0 392 546 A3 | 10/1990 |
| EP | 0 478 319 B1 | 4/1992 |
| EP | 0 514 927 A1 | 11/1992 |
| EP | 0 723 146 | 7/1996 |
| GB | 2 236 852 B | 4/1991 |
| WO | WO 89/11101 | 11/1989 |
| WO | WO 89/12695 A1 | 12/1989 |
| WO | WO 91/06678 | 5/1991 |
| WO | WO 93/02360 | 2/1993 |
| WO | WO 93/17126 A1 | 9/1993 |
| WO | WO 93/25563 A1 | 12/1993 |
| WO | WO 94/11530 | 5/1994 |
| WO | WO 94/23064 | 10/1994 |
| WO | WO 95/09248 | 4/1995 |
| WO | WO 95/35390 A1 | 12/1995 |
| WO | WO 96/03212 | 2/1996 |
| WO | WO 96/15271 A1 | 5/1996 |
| WO | WO 96/30392 A1 | 10/1996 |
| WO | WO 97/14028 | 4/1997 |
| WO | WO 97/31256 A2 | 8/1997 |
| WO | WO 97/40385 A1 | 10/1997 |
| WO | WO 97/46704 A1 | 12/1997 |
| WO | WO 98/13523 A1 | 4/1998 |
| WO | WO 98/31836 A1 | 7/1998 |
| WO | WO 98/40726 A1 | 9/1998 |
| WO | WO 98/50782 A2 | 11/1998 |
| WO | WO 98/53093 A1 | 11/1998 |
| WO | WO 98/53300 A2 | 11/1998 |
| WO | WO 99/18434 A1 | 4/1999 |
| WO | WO 99/60170 A1 | 11/1999 |
| WO | WO 99/64867 A1 | 12/1999 |
| WO | WO 99/67414 A1 | 12/1999 |
| WO | WO 99/67641 A2 | 12/1999 |
| WO | WO 00/04372 A1 | 1/2000 |
| WO | WO 00/13004 A2 | 3/2000 |
| WO | WO 00/16101 A2 | 3/2000 |
| WO | WO 00/39587 A1 | 7/2000 |
| WO | WO 00/47996 A2 | 8/2000 |
| WO | WO 00/48000 A1 | 8/2000 |
| WO | WO 00/58516 A2 | 10/2000 |
| WO | WO 00/63437 A2 | 10/2000 |
| WO | WO 00/71243 A1 | 11/2000 |
| WO | WO 00/71992 A1 | 11/2000 |
| WO | WO 00/71995 A2 | 11/2000 |
| WO | WO 00/75373 A2 | 12/2000 |

OTHER PUBLICATIONS

Anon., *Microphere Selection Guide*, Bangs Laboratories: Fishers, IN (Sep. 1998).
Bangs, L.B., "Immunological Applications of Microspheres," *The Latex Course*, Bangs Laboratories: Carmel, IN (Apr. 1996).
Barnard, S.M., et al., "A Fiber-Optic Chemical Sensor with Discrete Sensing Sites," *Nature* 353:338340 (Sep. 1991).
Brenner, et al., "Gene Expression Analysis by Massively Parallel Signature Sequencing (MPSS) on Micorbead Arrays," *Nature Biotech*. 18:630-634 (2000).
Chen, J., et al., "A Microsphere-Based Assay for Multiplexed Single Nucleotide Polymorphism Analysis Using Single Base Chain Extension," *Gen. Res*. 10(4):549-557 (Apr. 2000).
Church, et al., "Genomes for All," *Scientific American*, pp. 47-54 (Jan. 2005).
Czarnik, "Illuminating the SNP genomic code," *Mod. Drug Disc*. 1(2):49-55 (1998).
Drmanac, R., et al., "Prospects for a Miniaturized, Simplified and Frugal Human Genome Project," *Scientia Yugoslavica* 16(1-2):97-107 (1990).
Drmanac, R., et al., "Sequencing by Hybridization (SBH) with Oligonucleotide Probes as an Integral Approach for the Analysis of Complex Genomes," *Intl. J. Gen. Res*. 1(1):59-79 (1992).
Dramanac, R., et al., "Sequencing by Hybridization, "*Automated DNA Sequencing and Analysis*, Adams, M., et al. (eds.) 1994.
Drmanac, R. et al., Sequencing by Oligonucleotide Hybridization: A Promising Famework in Decoding of the Genome Program, *The 1st Intl. Conf. Electrophoresis Supercomputing and the Human Genome*, Proceeding of the Apr. 10-13, 1990 conference, Florida State University (Cantor, C., and Lim, H., eds.).
Dunn, et al., "Geneomic Signature Tags (GSTs): A System for Profiling Genomic DNA. Genome Research," pp. 1756-1765 (2002).
Ferguson, J.A., et al., "A fiber-optic DNA biosensor micorarray for the analysis of gene expression," *Nat. Biotechnol*. 14:1681-1684 (1996).
Freeman, T., et al., "Oxygen probe based on tetrakis(alkylamino)ethylene-Chemiluminescence," *Anal. Chem*. 53(1):98-102 (Jan. 1981).
Freifelder, D., "Fluorescence Spectroscopy," *Physical Biochemistry*, $2^{nd}$ ed., pp. 537-542, W.H. Freeman & Co.: San Francisco, CA (1982).
Fuh, M., et al., "Single Fibre Optic Fluorescence pH Probe." *Analyst* 112:1159-1163 (1987).
Healey, B., et al., "Development of a penicillin biosensor using a single optical imaging fiber," *SPIE Proc*. 2388:568-573 (1995).
Healey, B., et al., "Fiberoptic DNA Sensor Array Capable of Detecting Point Mutations," *Anal. Biochem*. 251:270-279 (1997).
Healey, B., et al., "Improved fiber-optic chemical sensor for penicillin," *Anal. Chem*. 67(24):4471-4476 (1995).
Hirschfeld, et al., "Laser Fiber-Optic 'Optrode' for Real Time In Vivo Blood Carbon Dioxide Level Monitoring," *J. Lightweave Technol*. LT-5(7):1027-1033 (1987).
Iannone, M., et al., "Multiplexed Single Nucleotide Polymorphism Genotyping by Oligonucleotide Ligation and Flow Cytometry," *Cytometry* 39(2):131-140 (Feb. 2000).

(56) References Cited

OTHER PUBLICATIONS

Jongeneel, et al., "Comprehensive Sampling of Gene Expression in Human Cell Lines with Massively Parallel Signature Sequencing," *PNAS* 100:4702-4705 (2003).
Jordan, D., et al., "Physiological pH Fiber Optic Chemical Sensor Based on Energy Transfer," *Anal. Chem.* 59(3):437-439 (Feb. 1987).
Lippitsch, M., et al., "Fibre-optic oxygen sensor with the fluorescence decay time as the information center," *Anal. Chim. Acta.* 205:1-6 (1998).
Lübbers, D., et al., "Optical Fluorescence Sensors for Continuous Measurement of Chemical Concentrations in Biological Systems," *Sens. Actuators* 4:641-654 (1983).
Lyamichev, V., et al., "Polymorphism identification and quantitative detection of genomic DNA by invasive cleavage of oligonucleotide probes," *Nat. Biotechnol.* 17:292-296 (1999).
Mignani, A.G., et al., "In vivo biomedical monitoring by fiber-optic systems," *J. Lightwave Technol.* 13(7):1396-1406 (1995).
Michael, K., et al., "Fabrication of micro- and nanostructures using optical imaging fibers and their use as chemical sensors," *Proc. 3rd Intl Symp., Microstructures and Micorfabricated Syst.*, P.J. Hesketh et al., (eds.), Electrochem. Soc. Proc. 97(5):152-157 (Aug. 1997).
Michael, K., et al., "Making sensors out of disarray: optical sensors microarrays," *Proc. SPIE* 3270:34-41 (1998).
Michael, K., et al., "Randomly ordered addressable high-density optical sensor arrays," *Anal. Chem.* 70(7):1242-1248 (Apr. 1998).
Milanovich, F., et al., "Clinical measurements using fiber optics and optrodes," *Novel Optical Fiber Techniques for Medical Applications*, A. Katzir (ed.) Proc. SPIE 494:18-24 (1984).
Munkholm, C., et al., "A Fiber optic sensor for $CO_2$ measurement," *Talanta* 35(2):109-112 (1988).
Munkholm, C., et al., "Polymer modification of fiber optic sensors as a method of enhancing fluorescence signal for pH measurement," *Anal. Chem.* 58(7):1427-1430 (Jun. 1986).
Pantano, P., et al., "Analytical applications of optical imaging fibers," *Anal. Chem.* 67:481A-487A (Aug. 1995).
Pantano, P., et al., "Ordered Nanowell Arrays," *Chem. Mater.* 8(12):2832-2835 (1996).
Peterson, J.I., et al., "Fiber optic pH probe for physiological use," *Anal. Chem.* 52(6):864-869 (May 1980).
Peterson, J.I., et al., "Fiber-optic sensors for biomedical applications," *Science* 224(4645):123-127 (Apr. 1984).
Piunno, P., et al., "Fiber-optic DNA sensor for fluorometric nucleic acid determination," *Anal. Chem.* 67(15):2635-2643 (Aug. 1995).
Pope, E., "Fiber optic chemical microsensors employing optically active silica microspheres," *SPIE* 2388:245-256 (1995).
Ronaghi, M., et al., "A Sequencing Method Based on Real-Time Pyrophosphate," *Science* 281:363-365 (1998).
Saari, L., et al., "pH sensor based on immobilized fluoresceinamine," *Anal. Chem.* 54(4):821-823 (Apr. 1982).
Schwab, S., et al., "Versatile, Efficient Raman Sampling with Fiber Optics," *Anal. Chem.* 56(12):2199-2204 (Oct. 1984).
Seitz, W.R., "Chemical sensors based on fiber optics," *Anal. Chem.* 56(1):16A-34A (Jan. 1984).
Seitz, W.R., "Chemical Sensors Based on Immobilized Indicators and Fiber Optics," *C.R.C. Crit. Rev. Anal. Chem.* 19(2):135-173 (1988).
Shendure, et al. "Accurate Multiplex Polony Sequencing of an Evolved Bacterial Genome," *Science* 309:1728-1732 (2005).
Shoemaker, D., et al., "Quantitative phenotypic analysis of yeast deletion mutants using a highly parallel molecular bar-coding strategy," *Nat. Genet.* 14(4):450-456 (Dec. 1996).
Strachan, N., et al., "A rapid general method for the identification of PCR products using a fibre-optic biosensor and its application to the detection of Listeria," *Lett. Appl. Microbiol.* 21(1):5-9 (Jul. 1995).
Walt, D., "Fiber Optic Imaging Sensors," *Acc. Chem. Res.* 31(5):267-278 (1998).
Walt, D., "Fiber-optic sensors for continuous clinical monitoring," *Proc. IEEE* 80(6):903-911 (1992).
Wolfbeis, O.S., "Fiber Optical Fluorosensors in Analytical and Clinical Chemistry," *Molecular Luminescence Spectroscopy, Methods and Applications*, Schulman (ed.), Wiley & Sons, New York, NY (1988).
Wolfbeis, O.S., et al., "Fiber-optic fluorosensor for oxygen and carbon dioxide," *Anal. Chem.* 60(19):2028-2030 (Oct. 1988).
Zhujun, Z., et al., "A Fluorescence Sensor for Quantifying pH in the Range for 6.5 to 8.5," *Anal. Chim. Acta.* 160:47-55 (1984).
Mag et al., "Synthesis and Selective Cleavage of an Oligodeoxynucleotide Containing a Bridged Non-Chiral Internucleotide 3'-Phosphoramidate Linkage", *Tetrahedron Letters* 33(48):7319-7322 (1992).
Abravaya et al., "Detection of point mutations with a modified ligase chain reaction (Gap-LCR)," *Nucleic Acids Research*, vol. 23, No. 4, p. 675-682 (1995).
Abravaya et al., "Detection of Point Mutations with Ligase Chain Reaction" ASM General Meeting of the American Society for Microbiology (Las Vegas, NV) 1994.
Abravaya et al., "Detection of Single Base Changes with GAP-LCR: Factors that Affect Discrimination," *Clin. Chem.*, vol. 40, No. 4 (1994).
Akane et al., "Direct Dideoxy Sequencing of Genomic DNA by Ligation-Mediated PCR," *BioTechniques*, vol. 16, No. 2, Jan. 1994.
Barany, "Genetic Disease Detection and DNA Amplification Using Cloned Thermostable Ligase," *Proc. Natl. Acad. Sci. USA*, vol. 88, p. 189-193, Jan. 1991.
Barany, "The Ligase Chain Reaction in a PCR World," *PCR Methods and Applications*, vol. 1, No. 1, p. 5-16, Aug. 1991.
Cahill et al., "Polymerase Chain Reaction and $Q\beta$ Replicase Amplification," *Clin. Chem.*, vol. 37, No. 9, p. 1482-1485 (1991).
Cantor et al., "Report on the Sequencing by Hybridization Workshop," *Genomics*, vol. 13, p. 1379-1383 (1992).
Cao, "Recent Developments in Ligase-Mediated Amplification and Detection," *TRENDS in Biotechnology*, vol. 22, No. 1, p. 38-44, Jan. 2004.
Carrino and Leffler, "Detection of HIV DNA Sequences Using the Ligase Chain Reaction (LCR)," *Clin. Chem.*, vol. 37, No. 6 (1991).
Carrino and Lee, "Nucleic acid amplification methods," *J. Microbiological Methods*, vol. 23, p. 3-20 (1995).
Chelly et al., "Transcription of the Dystrophin Gene in Human Muscle and Non-Muscle Tissues," *Nature*, vol. 333, No. 6167, p. 858-860, Jun. 30, 1988.
Day et al., "Detection of Steroid 21-Hydroxylase Alleles Using Gene-Specific PCR and a Multiplexed Ligation Detection Reaction," *Genomics*, vol. 29, p. 152-162 (1995).
Drmanac et al., "SBH and the Integration of Complementary Approaches in the Mapping, Sequencing, and Understanding of Complex Genomes," Technical Paper Presented at the International Conference on Bioinformatics, Supercomputing, and Complex Genome Analysis, St. Petersburg, FL (United States), Jun. 4-7, 1992.
Fainsod et al., "The homeo domain of a murine protein binds 5' to its own homeo box," *Proc. Natl. Acad. Sci. USA*, vol. 83, p. 9532-9536, Dec. 1986.
Gerry et al., "Universal DNA Microarray Method for Multiplex Detection of Low Abundance Point Mutations," *J. Mol. Biol.*, vol. 292, No. 2, p. 251-262 (1999).
Gilliland et al., "Analysis of cytokine mRNA and DNA: Detection and quantitation by competitive polymerase chain reaction," *Proc. Natl. Aca. Sci. USA*, vol. 87, p. 2725-2729, Apr. 1990.
Hsuih et al., "Novel, Ligation-Dependent PCR Assay for Detection of Hepatitis C Virus in Serum," *J. of Clin. Microbiology*, vol. 34, No. 3, p. 501-507, Mar. 1996.
John K. Elder, "Image Processing in Nucleic Acid Sequence Analysis," Thesis submitted for the degree of Doctor of Philosophy, Dept. of Biochemistry and Trinity College, University of Oxford (1993).
Khrapko et al., "A Method for DNA Sequencing by Hybridization with Oligonucleotide Matrix," *DNA Sequence—J.DNA Sequencing and Mapping*, vol. 1, p. 375-388 (1991).
Khrapko et al., "Hybridization of DNA with Oligonucleotides Immobilized in Gel: Convenient Method for Recording Individual Base Changes," *Molekulyamaya Biologiya*, vol. 25, No. 3, p. 718-730 (1991).

(56) References Cited

OTHER PUBLICATIONS

Kinzler and Vogelstein, "Whole genome PCR: application to the identification of sequences bound by gene regulatory proteins," *Nucleic Acids Research*, vol. 17, No. 10, p. 3645-3653 (1989).

Kramer and Lizardi, "Replicatable RNA reporters," *Nature*, vol. 339, p. 401-402, Jun. 1, 1989.

Laffler et al., "The ligase chain reaction in DNA-based diagnosis," *Ann. Biol. Clin.*, vol. 50, p. 821-826 (1993).

Landegren et al., "A Ligase-Mediated Gene Detection Technique," *Science*, vol. 241, No. 4862, p. 1077-1080, Aug. 26, 1988.

Lizardi and Kramer, "Exponential amplification of nucleic acids: new diagnostics using DNA polymerases and RNA replicases," *TIBTECH*, vol. 9, p. 53-58, Feb. 1991.

Luo et al., "Improving the fidelity of Thermus thermophilus DNA ligase," *Nucleic Acids Research*, vol. 24, No. 14, p. 3071-3078 (1996).

Lysov et al., "A New Method for Determining the DNA Nucleotide Sequence by Hybridization with Oligonucleotides," Translated from Doklady Akademii Nauk SSR, vol. 303, No. 6, pp. 1508-1511, Dec. 1988.

Maskos and Southern, "A study of oligonucleotide reassociation using large arrays of oligonucleotides synthesized on a glass support," *Nucleic Acids Research*, vol. 21, No. 20, p. 4663-4669 (1993).

McNamara et al., "Development of a Multiplex PCR-Ligase Detection Reaction Assay for Diagnosis of Infection by the Four Parasite Species Causing Malaria in Humans," *J. Clinical Microbiology*, p. 2403-2410, Jun. 2004.

Mirzabekov, "DNA Sequencing by Hybridization—a Megasequencing Method and a Diagnostic Tool?" *TIBTECH*, vol. 12, p. 27-32, Jan. 1994.

Nickerson et al., "Automated DNA diagnostics using an ELISA-based oligonucleotide ligation assay," *Proc. Natl. Acad. Sci. USA*, vol. 87, p. 8923-8927, Nov. 1990.

Nilsson et al., "Padlock Probes: Circularizing Oligonucleotides for Localized DNA Detection," *Science*, vol. 265, p. 2085-2088, Sep. 30, 1994.

Park, et al., "Detection of Hepatitis C Virus RNA Using Ligation-Dependent Polymerase Chain Reaction in Formalin-Fixed, Paraffin-Embedded Liver Tissues," *Am. J. of Pathology*, vol. 149, No. 5, p. 1485-1491, Nov. 1996.

Pfeifer et al., "Genomic Sequencing and Methylation Analysis by Ligation Mediated PCR," *Science*, vol. 246, p. 810-813, Oct. 6, 1989.

Punwaney et al., "Human Papillomavirus may be Common within Nasopharyngeal Carcinoma of Caucasian American: Investigation of Epstein-Barr Virus and Human Papillomavirus in Easterns and Western Nasopharyngeal Carcinoma Using Ligation-Dependent Polymerase Chain Reaction," *Head & Neck*, vol. 21, No. 1, p. 21-29, Jan. 1999.

Smith, "Ligation-mediated PCR of Restriction Fragments from Large DNA Molecules," *PCR Methods and Applications*, Aug. 1992, vol. 2, No. 1, p. 21-27.

Southern et al., "Analyzing and Comparing Nucleic Acid Sequences by Hybridization to Arrays of Oligonucleotides: Evaluation Using Experimental Models," *Genomics*, vol. 13, p. 1008-1017 (1992).

Strezoska et al., "DNA sequencing by hybridization: 100 bases read by a non-gel-based method," *Proc. Natl. Acad. Sci. USA*, vol. 88, p. 10089-10093, Nov. 1991.

U.S. Department of Energy, Office of Energy Research Grant Proposal, "Sequencing of DNA by Hybridization with oligonucleotides matrix (SHOM)," Mirzabekov (Principal Investigator), Mar. 30, 1992.

Wang et al., "Molecular Genetic and Genetic Correlations in Sodium Channelopathies: Lack of Founder Effect and Evidence for a Second Gene," *Am. J. Hum. Genet.*, vol. 52, p. 1074-1084 (1993).

Wiedmann et al. "Detection of *Listeria monocytogenes* with a Nonisotopic Polymerase Chain Reaction-Coupled Ligase Chain Reaction Assay," *Applied and Environmental Microbiology*, vol. 59, No. 8, p. 2743-2745, Aug. 1993.

Wiedmann et al., "Discrimination of Other *Listeria* Species by Ligase Chain Reaction," *Applied and Environmental Microbiology*, vol. 58, No. 11, p. 3443-3447, Nov. 1992.

Wiedmann et al., "Ligase Chain Reaction (LCR)—Overview and Applications," *PCR Methods and Applications*, vol. 3, No. 4, p. S51-S64, Feb. 1994.

Wilson et al., "Frequency of oncogenic point mutations in human tissues determined by combined PCR and LCR techniques," *Proceedings of the American Association for Cancer Research*, vol. 34, p. 262, Mar. 1993.

Wu and Wallace, "The Ligation Amplification Reaction (LAR)—Amplification of Specific DNA Sequences Using Sequential Rounds of Template-Dependent Ligation," *Genomics*, vol. 4, p. 560-569 (1989).

Yarkin et al., "Detection of HPV DNA in Cervical Specimens Collected in Cytologic Solution by Ligation-Dependent PCR," *J. of Clin. Cytology and Cytopathology*, May-vol. 47, No. 3, p. 450-456, Jun. 2003.

Hirschhorn, et al., "SBE-TAGS: An array-based method for efficient single-nucleotide polymorphism genotyping" *PNAS* (2000) 97(22): 12164-12169.

Ronaghi, et al., "Real-Time DNA Sequencing Using Detection of Pyrophosphate Release" *Analytical Biochemistry* (1996) 242: 84-89.

\* cited by examiner

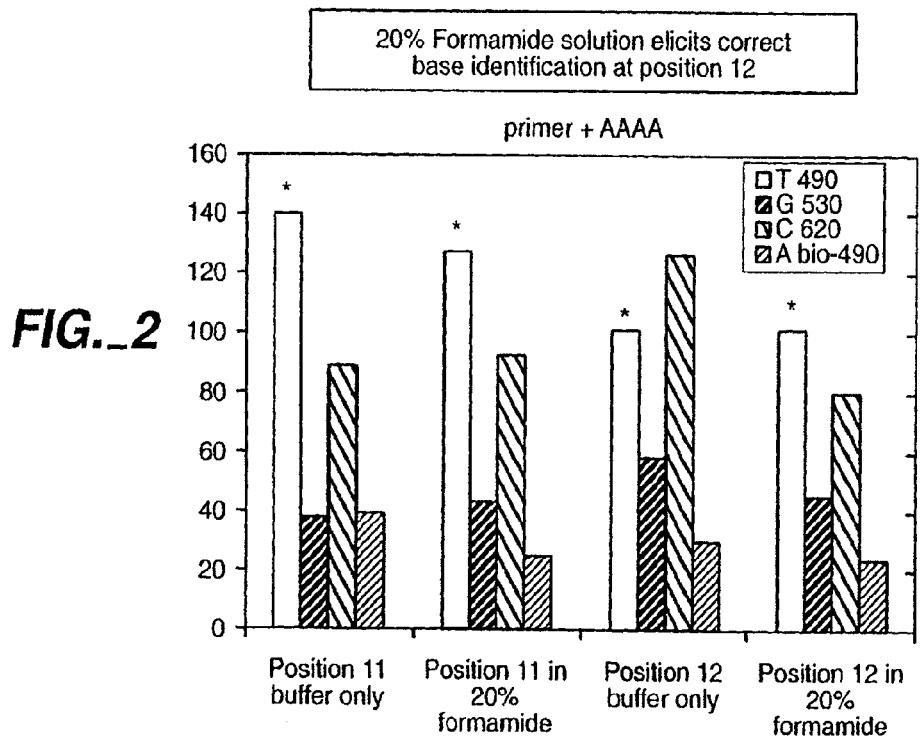

FIG._1

Correctly verified the identity of 14 probes using the same 4 target solutions

| Probes on bead | Name |
|---|---|
| GCG GTC CC AAAA | DC1 |
| GCG GTC CC GAAA | 9G |
| GCG GTC CC ACAA | 10C |
| GCG GTC CC CGAA | 9C10G |
| GCG GTC CC CAAA | 9C |
| GCG GTC CC TAAA | 9T |
| GCG GTC CC AGAA | 10G |
| GCG GTC CC ATAA | 10T |
| GCG GTC CC GCAA | 9G10C |
| GCG GTC CC TGAA | 9T10G |
| GCG GTC CC CCAA | 9C10C |
| GCG GTC CC CTAA | 9C10T |
| GCG GTC CC AAGA | 11G |
| GCG GTC CC AAAG | 12G |

T Cy5
G Cy3
C Fluorescein
A Biotin + St-Fl

FIG._2

20% Formamide solution elicits correct base identification at position 12

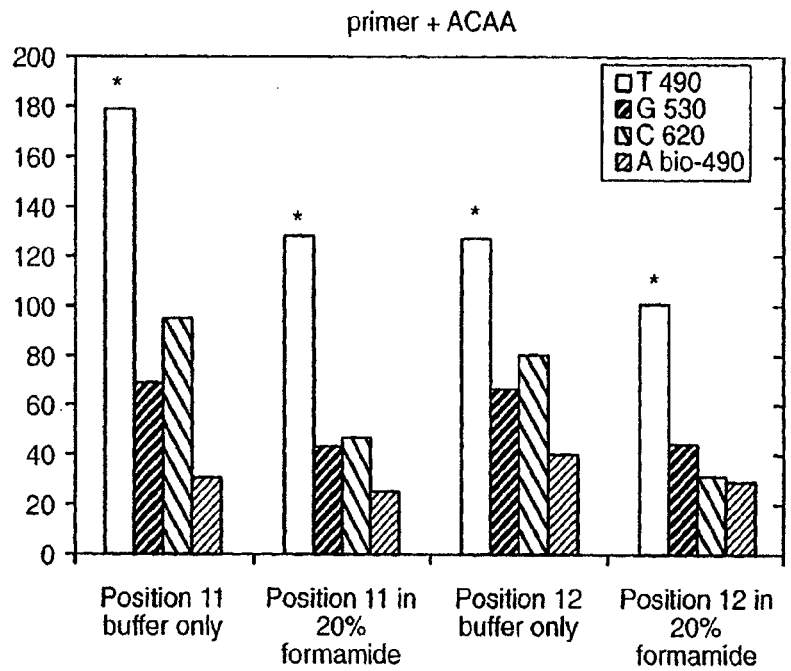
FIG._3
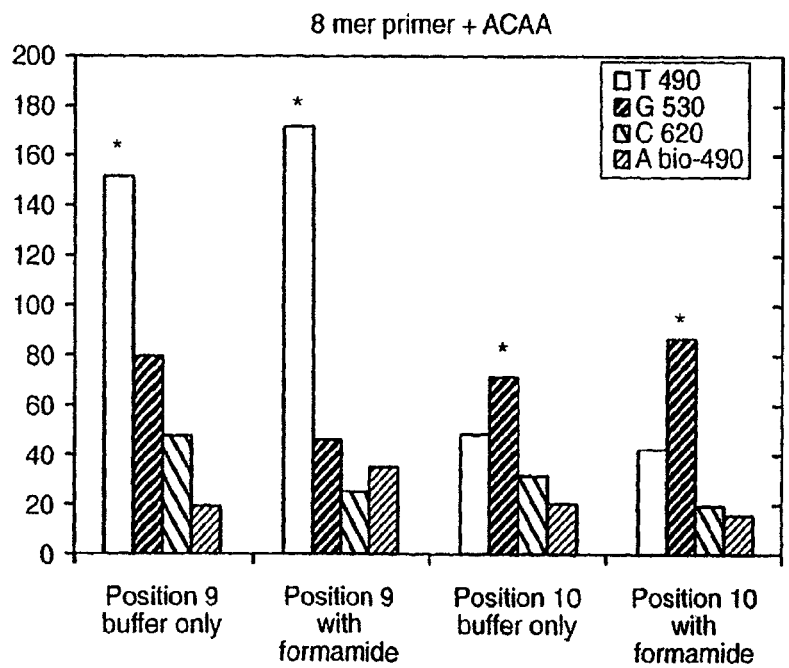
FIG._4

4 Different Probes Each on its own bead

| Bead | Probe | Name |
|---|---|---|
| Bead 1 | ○— GCG GTC CC AAAA (9 10 11 12) | DC1 |
| Bead 2 | ○— GCG GTC CC GAAA | 9G |
| Bead 3 | ○— GCG GTC CC ACAA | 10C |
| Bead 4 | ○— GCG GTC CC CGAA | 9C10G |

| Interrogate position 9 with 64 targets in solution | Interrogate position 10 with 64 targets in solution |
|---|---|
| ◇ CGC CAG GG TXXT | ◇ CGC CAG GG XTXT |
| ✺-CGC CAG GG CXXT | ✺-CGC CAG GG XCXT |
| ☆-CGC CAG GG GXXT | ☆-CGC CAG GG XGXT |
| ◁-CGC CAG GG AXXT | ◁-CGC CAG GG XAXT |

*FIG._5A*

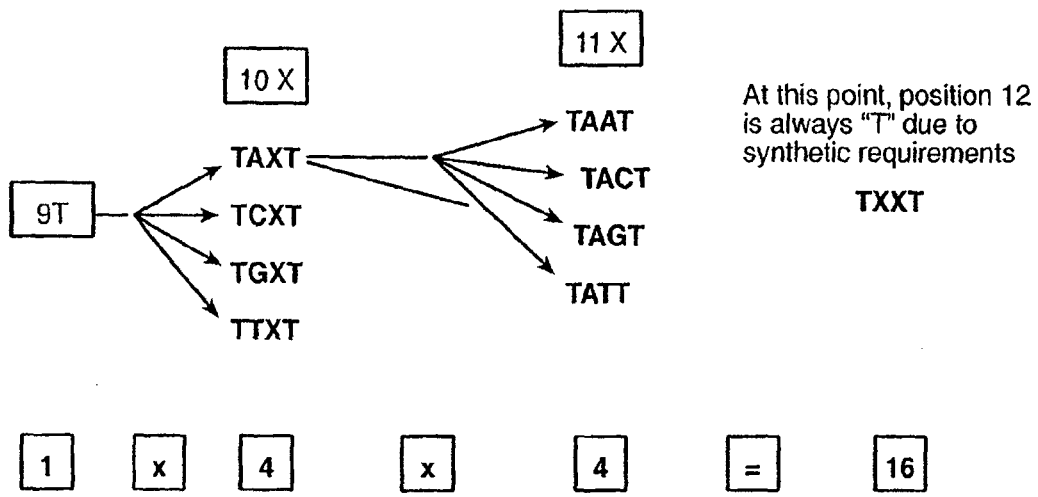
FIG._5B

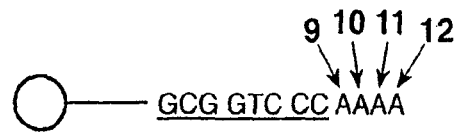

```
                              9 10 11 12
                              ↓ ↓  ↓  ↓
        ○———— GCG GTC CC AAAA
```

| Interrogate position 9 with 4 targets in solution | Interrogate position 10 with 4 targets in solution |
|---|---|
| ✧ CGC CAG GG TTTT | ✧ CGC CAG GG TTTT |
| ✺-CGC CAG GG CTTT | ✺-CGC CAG GG TCTT |
| ☆-CGC CAG GG GTTT | ☆-CGC CAG GG TGTT |
| ◁-CGC CAG GG ATTT | ◁-CGC CAG GG TATT |

| Interrogate position 11 with 4 targets in solution | Interrogate position 12 with 4 targets in solution |
|---|---|
| ✧ CGC CAG GG TTTT | ✧ CGC CAG GG TTTT |
| ✺-CGC CAG GG TTCT | ✺-CGC CAG GG TTTC |
| ☆-CGC CAG GG TTGT | ☆-CGC CAG GG TTTG |
| ◁-CGC CAG GG TTAT | ◁-CGC CAG GG TTTA |

FIG._5C

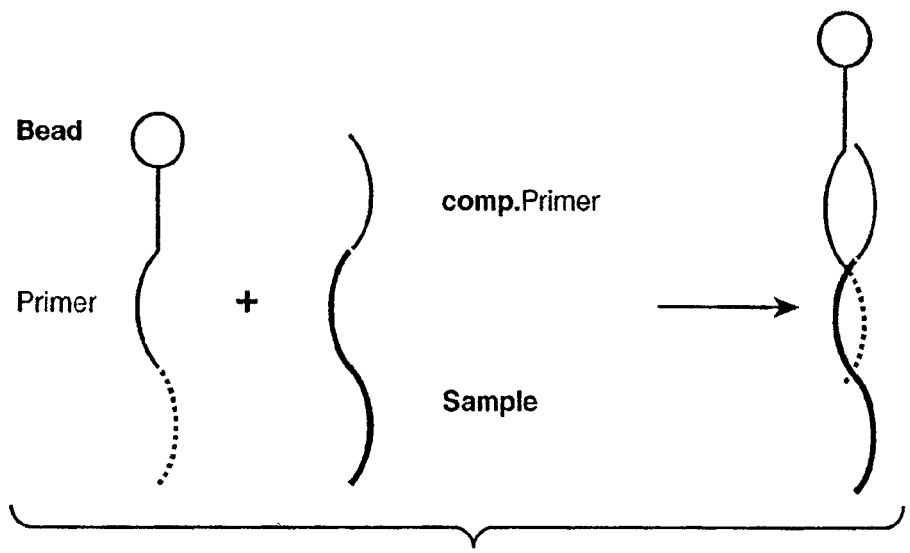

COMBINATORIAL DECODING OF RANDOM NUCLEIC ACID ARRAYS

RELATED APPLICATIONS

This application is a continuation of U.S. patent application Ser. No. 13/159,302, filed Jun. 13, 2011, which is a continuation of Ser. No. 12/506,116, filed Jul. 20, 2009, now U.S. Pat. No. 7,960,119, issued Jun. 14, 2011, which is a continuation of U.S. patent application Ser. No. 11/625,708, filed Jan. 22, 2007, now U.S. Pat. No. 7,563,576, issued Jul. 21, 2009, which is a continuation of U.S. patent application Ser. No. 10/648,848, filed Aug. 21, 2003, now U.S. Pat. No. 7,166,431, issued Jan. 23, 2007, which is a division of U.S. patent application Ser. No. 09/574,117, filed May 19, 2000, now U.S. Pat. No. 6,620,584, issued Sep. 16, 2003, which claims priority from U.S. Provisional Patent Application No. 60/135,052, filed May 20, 1999.

FIELD OF THE INVENTION

The invention relates to compositions and methods for decoding microsphere array sensors.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

Of particular use in these sensors are detection mechanisms utilizing luminescence. Recently, the use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in *C.R.C. Critical Reviews In Analytical Chemistry*, Vol. 19, 1988, pp. 135-173; Wolfbeis, O. S., "Fiber Optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2 (4):38 (1987); Walt, et al., "Chemical Sensors and Microinstrumentation", *ACS Symposium Series*, Vol. 403, 1989, p. 252, and Wolfbeis, O. S., *Fiber Optic Chemical Sensors*, Ed. CRC Press, Boca Raton, Fla., 1991, 2nd Volume.

When using an optical fiber in an in vitro/in vivo sensor, one or more light absorbing dyes are located near its distal end. Typically, light from an appropriate source is used to illuminate the dyes through the fiber's proximal end. The light propagates along the length of the optical fiber; and a portion of this propagated light exits the distal end and is absorbed by the dyes. The light absorbing dye may or may not be immobilized; may or may not be directly attached to the optical fiber itself; may or may not be suspended in a fluid sample containing one or more analytes of interest; and may or may not be retainable for subsequent use in a second optical determination.

Once the light has been absorbed by the dye, some light of varying wavelength and intensity returns, conveyed through either the same fiber or collection fiber(s) to a detection system where it is observed and measured. The interactions between the light conveyed by the optical fiber and the properties of the light absorbing dye provide an optical basis for both qualitative and quantitative determinations.

Of the many different classes of light absorbing dyes which conventionally are employed with bundles of fiber strands and optical fibers for different analytical purposes are those more common compositions that emit light after absorption termed "fluorophores" and those which absorb light and internally convert the absorbed light to heat, rather than emit it as light, termed "chromophores."

Fluorescence is a physical phenomenon based upon the ability of some molecules to absorb light (photons) at specified wavelengths and then emit light of a longer wavelength and at a lower energy. Substances able to fluoresce share a number of common characteristics: the ability to absorb light energy at one wavelength $\lambda_{ab}$; reach an excited energy state; and subsequently emit light at another light wavelength, $\lambda_{em}$. The absorption and fluorescence emission spectra are individual for each fluorophore and are often graphically represented as two separate curves that are slightly overlapping. The same fluorescence emission spectrum is generally observed irrespective of the wavelength of the exciting light and, accordingly, the wavelength and energy of the exciting light may be varied within limits; but the light emitted by the fluorophore will always provide the same emission spectrum. Finally, the strength of the fluorescence signal may be measured as the quantum yield of light emitted. The fluorescence quantum yield is the ratio of the number of photons emitted in comparison to the number of photons initially absorbed by the fluorophore. For more detailed information regarding each of these characteristics, the following references are recommended: Lakowicz, J. R., *Principles of Fluorescence Spectroscopy*, Plenum Press, New York, 1983; Freifelder, D., Physical Biochemistry, second edition, W. H. Freeman and Company, New York, 1982; "Molecular Luminescence Spectroscopy Methods and Applications: Part I" (S. G. Schulman, editor) in *Chemical Analysis, vol. 77*, Wiley & Sons, Inc., 1985; *The Theory of Luminescence*, Stepanov and Gribkovskii, Iliffe Books, Ltd., London, 1968.

In comparison, substances which absorb light and do not fluoresce usually convert the light into heat or kinetic energy. The ability to internally convert the absorbed light identifies the dye as a "chromophore." Dyes which absorb light energy as chromophores do so at individual wavelengths of energy and are characterized by a distinctive molar absorption coefficient at that wavelength. Chemical analysis employing fiber optic strands and absorption spectroscopy using visible and ultraviolet light wavelengths in combination with the absorption coefficient allow for the determination of concentration for specific analyses of interest by spectral measurement. The most common use of absorbance measurement via optical fibers is to determine concentration which is calculated in accordance with Beers' law; accordingly, at a single absorbance wavelength, the greater the quantity of the composition which absorbs light energy at a given wavelength, the greater the optical density for the sample. In this way, the total quantity of light absorbed directly correlates with the quantity of the composition in the sample.

Many of the recent improvements employing optical fiber sensors in both qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations and applications such as pH measurement, oxygen detection, and carbon dioxide analyses. These developments are exemplified by the following publications: Freeman, et al., *Anal Chem.* 53:98 (1983); Lippitsch et al., *Anal. Chem. Acta.* 205:1, (1988); Wolfbeis et al., *Anal. Chem.* 60:2028 (1988); Jordan, et al., *Anal. Chem.* 59:437 (1987); Lubbers et al., *Sens. Actuators* 1983; Munkholm et al., *Talanta* 35:109 (1988); Munkholm et al., *Anal. Chem.* 58:1427 (1986); Seitz, W. R., *Anal. Chem.* 56:16 A-34A (1984); Peterson, et al., *Anal. Chem.* 52:864 (1980): Saari, et al., *Anal. Chem.* 54:821 (1982); Saari, et al., *Anal. Chem.* 55:667 (1983); Zhujun et al., *Anal. Chem. Acta.* 160: 47 (1984); Schwab, et al., *Anal. Chem.* 56:2199 (1984); Wolfbeis, O. S., "Fiber Optic Chemical Sensors", *Ed. CRC Press*, Boca Raton, Fla., 1991, 2nd Volume; and Pantano, P., Walt, D. R., *Anal. Chem.*, 481A-487A, Vol. 67, (1995).

More recently, fiber optic sensors have been constructed that permit the use of multiple dyes with a single, discrete fiber optic bundle. U.S. Pat. Nos. 5,244,636 and 5,250,264 to Walt, et al. disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

U.S. Pat. No. 6,023,540 and U.S. Ser. No. 09/151,877 describe array compositions that utilize microspheres or beads on a surface of a substrate, for example on a terminal end of a fiber optic bundle, with each individual fiber comprising a bead containing an optical signature. Since the beads are placed randomly, a unique optical signature is needed to "decode" the array; i.e. after the array is made, a correlation of the location of an individual site on the array with the bead or bioactive agent at that particular site can be made. This means that the beads may be randomly distributed on the array, a fast and inexpensive process as compared to either the in situ synthesis or spotting techniques of the prior art. Once the array is loaded with the beads, the array can be decoded, or can be used, with full or partial decoding occurring after testing, as is more fully outlined below.

One drawback with the previous system is that it requires a set of unique optical signatures. While large sets of such signatures are available, for example by using different ratios of different dyes, it would be preferable to use decoding systems that do not rely on the use of sets of optical signatures. Accordingly, it is an object of the invention to provide methods to allow decoding of bead arrays without relying solely on unique optical signatures.

SUMMARY OF THE INVENTION

In accordance with the objects outlined above, the present invention provides compositions comprising a plurality of nucleic acids, each nucleic acid comprising an invariant sequence, a variable sequence and a label. In addition, the invention provides a method for decoding an array composition. The method includes providing an array composition comprising a substrate with a surface comprising discrete sites and a population of microspheres comprising first and second subpopulations, each subpopulation comprising an identifier nucleic acid sequence comprising a primer sequence and a decoder sequence. The method further comprises adding to the array a first set of combinatorial decoding probes comprising a priming sequence, at least one decoding nucleotide and a label, and detecting the presence of the label. In addition the invention provides kits comprising a substrate comprising a surface with discrete sites, a population of microspheres and a decoder probe composition comprising a plurality of probes.

BRIEF DESCRIPTION OF THE DRAWINGS

FIG. 1 (SEQ ID NOS: 1-14) depicts the sequence of 14 probes attached to beads.

FIG. 2 is a graph depicting that 20% formamide elicits correct base identification at the terminal position, position 12, of immobilized probes. The star indicates the correct base identification.

FIG. 3 is a graph depicting that the correct identification of the bases at position 11 and 12 (the terminal and terminal-1 positions) is achieved via competition using 20% formamide in the hybridization buffer.

FIG. 4 is a graph depicting that the correct identification of the bases at internal positions (internal positions of the immobilized probes) is achieved via competition in the hybridization buffer.

FIGS. 5A (SEQ ID NOS: 1-14 and 15-22), 5B (SEQ ID NOS: 15-18), 5C (SEQ ID NOS: 19-31) schematically depict 4 different probes each on its own bead, and solution target probes to interrogate different positions of the bead-bound probe. The symbols schematically depict different labels.

FIG. 6 (SEQ ID NO: 32) depicts a method of using a DNA array to sequence.

FIG. 7 (SEQ ID NO: 1) schematically depicts a decoding scheme.

DETAILED DESCRIPTION OF THE INVENTION

The present invention is generally based on previous work comprising a bead-based analytic chemistry system in which beads, also termed microspheres, carrying different chemical functionalities are distributed on a substrate comprising a patterned surface of discrete sites that can bind the individual microspheres. Since the beads are generally placed onto the substrate randomly, the previous work relied on the incorporation of unique optical signatures, generally fluorescent dyes, that could be used to identify the chemical functionality on any particular bead. This allows the synthesis of the candidate agents (i.e. compounds such as nucleic acids and antibodies) to be divorced from their placement on an array, i.e. the candidate agents may be synthesized on the beads, and then the beads are randomly distributed on a patterned surface. Since the beads are first coded with an optical signature, this means that the array can later be "decoded", i.e. after the array is made, a correlation of the location of an individual site on the array with the bead or candidate agent at that particular site can be made. This means that the beads may be randomly distributed on the array, a fast and inexpensive process as compared to either the in situ synthesis or spotting techniques of the prior art.

There are a number of ways that the arrays can be either precoded or later decoded. These techniques are generally described in U.S. Ser. Nos. 09/189,543; 08/944,850, 09/033, 462 and 09/151,877 and PCT applications US98/05025 and US98/21193, all of which are expressly incorporated herein by reference. That is, as will be appreciated by those in the art, the placement of the bioactive agents is generally random, and thus a coding/decoding system is required to identify the bioactive agent at each location in the array. This may be done in a variety of ways, as is more fully outlined below, and generally includes: a) coding techniques, such as the use of unique optical signatures for each type of bead; b) the use of decoding binding ligands (DBLs), generally directly labeled, that binds to either the bioactive agent or to identifier binding ligands (IBLs) attached to the beads; c) positional decoding, for example by either targeting the placement of beads (for example by using photoactivatible or photocleavable moieties to allow the selective addition of beads to particular locations), or by using either sub-bundles or selective loading of the sites, as are more fully outlined below; d) selective decoding, wherein only those beads that bind to a target are decoded; or e) combinations of any of these. In some cases, as is more fully outlined below, this decoding may occur for all the beads, or only for those that bind a particular target analyte. Similarly, this may occur either prior to or after addition of a target analyte.

Once the identity of the bioactive agent and its location of each microsphere in the array has been fixed, the array is exposed to samples containing the target analytes, although as outlined below, this can be done prior to or during the analysis as well. The target analytes will bind to the bioactive agents as is more fully outlined below, and results in a change in the optical signal of a particular bead.

In the present invention, "decoding" does not rely solely on the use of optical signatures (although as described herein, the use of beads with optical signatures can allow the "reuse" of the decoding probes), but rather on the use of combinatorial decoding nucleic acids that are added during a decoding step. The decoding nucleic acids will hybridize either to a distinct identifier coding nucleic acid (identifier probe) that is placed on the beads, or to the bioactive agent itself, for example when the bioactive agent is a nucleic acid, at least some portion of which is single stranded to allow hybridization to a decoding probe. The decoding nucleic acids are either directly or indirectly labeled, and thus decoding occurs by detecting the presence of the label.

As is more fully outlined below, the combinatorial decoding works as follows. The coding nucleic acids (also termed identifier probes (IP) or identifier nucleic acids) comprise a primer sequence and an adjacent decoding sequence. Each decoder (or decoding) probe comprises a priming sequence (sometimes referred to herein as an "invariant sequence"), that will hybridize to the primer sequence, and at least one decoding nucleotide, generally contained within a variable seqeunce. The decoder probes are made as sets, with each set generally comprising at least four subsets that each have a different decoding nucleotide at the same position i.e. the detection position, (i.e. adenine, thymidine (or uracil, as desired), cytosine and guanine), with each nucleotide at the detection position (detection nucleotide) comprising a unique label, preferably a fluorophore. The decoder probes are added under conditions that allow discrimination of perfect complementarity and imperfect complementarity. Thus, the decoding probe that comprises the correct base for basepairing with the coding nucleotide being interrogated will hybridize the best, and the other three decoding probes will be washed away. The detection of the unique fluor associated with the detection nucleotide allows the identification of the coding nucleotide at that position. By repeating these steps with a new set of decoding probes that extends the position of the detection nucleotide by one base, the identity of next coding nucleotide is elucidated. Although such a decoding system may require the use of large numbers of different decoding probes, synthesis of the probes is dramatically facilitated by the use of split and mix combinatorial synthesis as described below.

Accordingly, the present invention provides array compositions comprising at least a first substrate with a surface comprising individual sites. By "array" herein is meant a plurality of candidate agents in an array format; the size of the array will depend on the composition and end use of the array. Arrays containing from about 2 different bioactive agents (i.e. different beads) to many millions can be made, with very large fiber optic arrays being possible. Generally, the array will comprise from two to as many as a billion or more, depending on the size of the beads and the substrate, as well as the end use of the array. Thus very high density, high density, moderate density, low density and very low density arrays may be made. Preferred ranges for very high density arrays are from about 10,000,000 to about 2,000,000,000 (all numbers are per square cm), with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 µm or less (with beads of 200 nm possible) can be used, and very small fibers are known, it is possible to have as many as 40,000 or more (in some instances, 1 million) different fibers and beads in a 1 mm$^2$ fiber optic bundle, with densities of greater than 15,000,000 individual beads and fibers (again, in some instances as many as 25-50 million) per 0.5 cm$^2$ obtainable.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

In a preferred embodiment, the substrate is an optical fiber bundle or array, as is generally described in U.S. Ser. Nos. 08/944,850, 09/287,573, 08/519,062 and 09/340,350, PCT U898/05025, PCT US98/09163, and PCT US99/19624, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

At least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the association of beads at any position. That is, the surface of the substrate is modified to allow association of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle, as is generally described in Ser. Nos. 08/818,199, 09/151,877, 09/450,829, PCT US98/05025 and PCT/US99/20914 all of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically' modified sites, that can be used to associate, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic association of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydro affinity. For example, the use of hydrophobic sites with hydrophobic beads, in an aqueous system, drives the association of the beads preferentially onto the sites. As outlined above, "pattern" in this sense includes the use of a uniform treatment of the surface to allow association of the beads at discrete sites, as well as treatment of the surface resulting in discrete sites. As will be appreciated by those in the art, this may be accomplished in a variety of ways.

Other configurations of substrates are described in 60/113, 968, PCT/US99/31022, Ser. Nos. 09/256,943, 09/473,904 and 09/316,154 all of which are hereby expressly incorporated by reference.

The compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and Teflon may all be used. "*Microsphere Detection Guide*" from Bangs Laboratories, Fishers IN is a helpful guide.

The beads need not be spherical; irregular particles may be used. In addition, the beads may be porous, thus increasing the surface area of the bead available for either bioactive agent attachment or coding nucleic acid attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a bioactive agent, although as will be appreciated by those in the art, there may be some microspheres which do not contain a bioactive agent, depending on the synthetic methods. By "candidate bioactive agent" or "bioactive agent" or "chemical functionality" or "binding ligand" herein is meant as used herein describes any molecule, e.g., protein, oligopeptide, small organic molecule, coordination complex, polysaccharide, polynucleotide, etc. which can be attached to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 Daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and proteins.

Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents are used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an inter-action library, nature provides a hint with the immune response: a diversity of $10^7$-$10^8$ different antibod-ies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least $10^9$ different bioactive agents are simultaneously analyzed in the subject methods. Preferred methods maximize library size and diversity.

In a preferred embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids (generally called "probe nucleic acids" or "candidate probes" herein). By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10): 1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowski, et al., Angew. Chem. Intl. Ed. English, 30:423 (1991); Letsinger, et al., J. Am. Chem. Soc., 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments; for example, PNA is particularly preferred. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), etc. In a preferred embodiment, the nucleic acid preferably includes at least one universal base. Universal bases are those that can substitute for any of the five natural bases, that is, universal bases will basepair with all natural bases, preferably equally well. Suitable universal bases include, but are not limited to, inosine, hypoxanthine, 5-nitroindole, acylic 5-nitroindole, 4-nitropyrazole, 4-nitroimidazole and 3-nitropyrrole. See Loakes et al., Nucleic Acid Res. 22:4039 (1994); Van Aerschot et al., Nucleic Acid Res. 23:4363 (1995); Nichols et al., Nature 369:492 (1994); Berstrom et al., Nucleic Acid Res. 25: 1935 (1997); Loakes et al., Nucleic Acid Res. 23:2361 (1995); Loakes et al., J. Mol. Biol. 270:426 (1997); and Fotin et al., Nucleic Acid Res. 26:1515 (1998); and references cited therein, all of which are expressly incorporated by reference.

In a preferred embodiment, the bioactive agents are libraries of clonal nucleic acids, including DNA and RNA. In this embodiment, individual nucleic acids are prepared, generally using conventional methods (including, but not limited to, propagation in plasmid or phage vectors, amplification techniques including PCR, etc.). The nucleic acids are preferably arrayed in some format, such as a microtiter plate format, and beads added for attachment of the libraries.

Attachment of the clonal libraries (or any of the nucleic acids outlined herein) may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc.

In a preferred embodiment, affinity capture is used to attach the clonal nucleic acids to the beads. For example, cloned nucleic acids can be derivatized, for example with one member of a binding pair, and the beads derivatized with the other member of a binding pair. Suitable binding pairs are as described herein for identifier/decoder probe pairs. For example, the cloned nucleic acids may be biotinylated (for example using enzymatic incorporate of biotinylated nucleotides, for by photoactivated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

Similarly, affinity capture utilizing hybridization can be used to attach cloned nucleic acids to beads. For example, as is known in the art, polyA+RNA is routinely captured by hybridization to oligo-dT beads; this may include oligo-dT capture followed by a cross-linking step, such as psoralen crosslinking). If the nucleic acids of interest do not contain a polyA tract, one can be attached by polymerization with terminal transferase, or via ligation of an oligoA linker, as is known in the art.

Alternatively, chemical crosslinking may be done, for example by photoactivated crosslinking of thymidine to reactive groups, as is known in the art.

As described above generally for proteins, nucleic acid bioactive agents may be naturally occurring nucleic acids, random nucleic acids, or "biased" random nucleic acids. For example, digests of prokaryotic or eukaryotic genomes may be used as is outlined above for proteins.

In general, probes of the present invention are designed to be complementary to a target sequence (either the target analyte sequence of the sample or to other probe sequences, as is described herein), such that hybridization of the target and the probes of the present invention occurs.

In some embodiments, this complementarity is preferably perfect. For example, as is more fully outlined below, the decoding probes are designed to allow discrimination between perfect complementarity and mismatches at the decoding position. Therefore, the decoding probes of the invention preferably contain no mismatches.

However, for other embodiments, and in some cases for non-decoding position decoding probes, this complementarity need not be perfect; there may be any number of base pair mismatches that will interfere with hybridization between the probes and their target sequences. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions. High stringency conditions are known in the art; see for example Maniatis et al., Molecular Cloning; A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide, In another embodiment, less stringent hybridization conditions are used; for example, moderate or low stringency conditions may be used, as are known in the art; see Maniatis and Ausubel, supra, and Tijssen, supra.

The term 'target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent.

As will be appreciated by those in the art, the bioactive agents may either be synthesized directly on the beads, or they may be made and then attached after synthesis. In a preferred embodiment, linkers are used to attach the bioactive agents to the beads, to allow both good attachment, sufficient flexibility to allow good interaction with the target molecule, and to avoid undesirable binding reactions.

In a preferred embodiment, the bioactive agents are synthesized directly on the beads. As is known in the art, many classes of chemical compounds are currently synthesized on solid supports, including beads, such as peptides, organic moieties, and nucleic acids.

In a preferred embodiment, the bioactive agents are synthesized first, and then covalently attached to the beads. As will be appreciated by those in the art, this will be done depending on the composition of the bioactive agents and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155-200, incorporated herein by reference) which can be used to attach cysteine containing proteinaceous agents to the support. Alternatively, an amino group on the candidate agent may be used for attachment to an amino group on the surface. For example, a large number of stable bifunctional groups are well known in the art, including homo bifunctional and heterobifunctional linkers (see Pierce Catalog and Handbook, pages 155-200). In an additional embodiment, carboxyl groups (either from the surface or from the candidate agent) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems.* 7(4):275.308 (1991), expressly incorporated herein). Proteinaceous candidate agents may also be attached using other techniques known in the art, for example for the attachment of antibodies to polymers; see Slinkin et al., *Bioconj Chem.* 2:342-348 (1991); Torchilin et al., supra; Trubetskoy et al., *Bioconj. Chem.*

3:323-327 (1992); King et al., *Cancer Res.* 54:6176-6185 (1994); and Wilbur et al., *Bioconjugate Chem.* 5:220-235 (1994), all of which are hereby expressly incorporated by reference). It should be understood that the candidate agents may be attached in a variety of ways, including those listed above. Preferably, the manner of attachment does not significantly alter the functionality of the candidate agent; that is, the candidate agent should be attached in such a flexible manner as to allow its interaction with a target.

Specific techniques for immobilizing enzymes on microspheres are known in the prior art. In one case, $NH_2$ surface chemistry microspheres are used. Surface activation is achieved with a 2.5% glutaraldehyde in phosphate buffered saline (10 mM) providing a pH of 6.9. (138 mM NaCl, 2.7 mM, KCl). This is stirred on a stir bed for approximately 2 hours at room temperature. The microspheres are then rinsed with ultrapure water plus 0.01% tween 20 (surfactant)-0.02%, and rinsed again with a pH 7.7 PBS plus 0.01% tween 20. Finally, the enzyme is added to the solution, preferably after being prefiltered using a 0.45 µm amicon micropure filter.

In a preferred embodiment, the microspheres additionally comprise identifier nucleic acids for use in the combinatorial decoding system of the invention.

Generally, the identifier probes (IP) and decoder probes (DP) range from about 4 basepairs in length to about 1000, with from about 6 to about 100 being preferred, and from about 8 to about 40 being particularly preferred. What is important is that the probes are long enough to be specific, i.e. to distinguish between different IP-DP pairs, yet short enough to allow both a) dissociation, if necessary, under suitable experimental conditions, and b) efficient hybridization.

In a preferred embodiment, as outlined above, each subpopulation of beads comprises identifier probes (which may be the candidate agents or not) that comprise a primer sequence and a decoding sequence adjacent to the primer sequence. By "primer sequence" herein is meant a nucleic acid sequence that is long enough to allow hybridization of a decoder probe in a sequence specific manner. Generally, the primer sequences range from about 2 to about 50 basepairs, with from about 4 to about 40 being preferred, and from about 5 to about 20 being particularly preferred.

In a preferred embodiment, the primer sequence is the same for all identifier probes in the array. In an additional preferred embodiment, different sets of primers are used in an array.

Directly adjacent to the primer sequence in the identifier probe is the decoding sequence. By "decoding sequence" herein is meant the nucleic acid which identifies the candidate agent on the bead. That is, the identity of the candidate agent on the bead must be correlated to a position on the array, and this is done using the decoding sequence, that is either itself the candidate agent or it identifies the candidate agent. At the time the array is made, the decoding sequence on any particular bead is unknown, and must be elucidated as described herein.

The length of the decoding sequence will vary with the size of the array and its purpose. For example, when the identifier probes are different from the candidate agents, the number of different "codes" will depend on the size of the array. Thus, for an array size of 1000, the decoding sequences must be 5 nucleotides long ($4^5=1024$) to ensure a unique decoding sequence for each candidate agent. In a preferred embodiment the decoding sequence contains from 1 to 1000 nucleotides; in a particularly preferred embodiment, the decoding sequence contains from 1 to 100 nucleotides in a most preferred embodiment the decoding sequence contains from 1 to 20 nucleotides.

When the decoding sequence is the candidate agent, the length of the decoding sequence will depend on the use of the array and the required level of specificity of the probes for a particular target sequence, as is generally outlined above.

In a preferred embodiment, the identifier probe is first synthesized and then attached to the beads. In this embodiment, the beads are first functionalized as described herein, to allow for attachment of the nucleic acids. In one embodiment, the beads may comprise a linker (or adapter) sequence to which the coding probe hybridizes. Examples of adapters are disclosed in U.S. Ser. Nos. 60/135,123 and 60/160,917, both of which are expressly incorporated herein by reference.

In an alternative embodiment, the identifier probe is synthesized directly on the beads. In this embodiment, the beads are first functionalized with an anchor sequence and then carried through a split and mix synthesis to create all possible n-mers in the bead library.

In a preferred embodiment, the primer sequence is first attached to or synthesized on the beads. Following this, the decoding sequence is synthesized by split and mix synthesis. An example is illustrative of the system.

As demonstrated below, the beads are first functionalized with the primer sequence (SUVWXYZ) and then carried through a split and mix synthesis to create all possible n-mers as probes on the bead library.

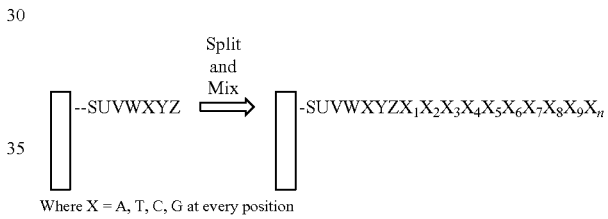

Where X = A, T, C, G at every position

This type of probe set is universal in that any target sequence can in principle be analyzed. In a preferred embodiment the probes are used to decode an array as described herein.

There are various difficulties with the approach that have previously hindered its effective implementation. Primarily, the number of probes required scales exponentially with probe length. For example, to represent each possible nucleic acid of a combinatorial probe of 8 nucleotides in length would require the synthesis of 65,356 nucleic acids. However, by the use of the split and mix combinatorial synthesis, synthesizing this number of nucleic acids requires only eight steps. That is, to synthesize probes of length n requires at least 4n reactions, and generates $4^n$ sequences (Table 1). However, as each of 4 nucleotides are reacted simultaneously (yet independently) in each step, the number of steps required to synthesize a vast number of probes is minimized.

TABLE 1

The number of unique probe sequences scales exponentially with probe length.

| Probe Length = Synthesis Steps | Synthesis Reactions | Number of Probes |
|---|---|---|
| n | 4n | $4^n$ |
| 4 | 16 | 256 |
| 8 | 32 | 65,536 |
| 10 | 40 | 1,048,576 |

TABLE 1-continued

The number of unique probe sequences scales exponentially with probe length.

| Probe Length = Synthesis Steps | Synthesis Reactions | Number of Probes |
|---|---|---|
| 15 | 60 | $1.07 \times 10^9$ |
| 20 | 80 | $1.10 \times 10^{12}$ |

As can be seen from the table, although the number of probes in a universal set can be very large, the actual number of synthetic steps is quite small. This means that the probe libraries can be synthesized on a large scale in a very efficient manner. Importantly, if the synthesis is truly combinatorial, and all probe sequences are made, then no complex masking strategies are required. Entirely straightforward large-scale combinatorial synthesis techniques can be used to make sufficient beads to assemble effectively limitless numbers of arrays relatively cheaply, creating the potential for widespread dissemination of the technology.

In addition, decoding of the array, i.e., elucidation of the identity of the identifier probe also is accomplished with a combinatorially prepared library. That is, sets of decoding probes as described herein are synthesized. In a preferred embodiment, the decoding probes are synthesized using the split and mix synthesis approach.

In a preferred embodiment, the microspheres do not contain an optical signature. That is, as outlined in U.S. Pat. No. 6,023,540 and U.S. Ser. No. 09/151,877, previous work had each subpopulation of microspheres comprising a unique optical signature or optical tag that is used to identify the unique bioactive agent of that subpopulation of microspheres; that is, decoding utilizes optical properties of the beads such that a bead comprising the unique optical signature may be distinguished from beads at other locations with different optical signatures. Thus the previous work assigned each bioactive agent a unique optical signature such that any microspheres comprising that bioactive agent are identifiable on the basis of the signature. These optical signatures comprised dyes, usually chromophores or fluorophores, that were entrapped or attached to the beads themselves. Diversity of optical signatures utilized different fluorochromes, different ratios of mixtures of fluorochromes, and different concentrations (intensities) of fluorochromes.

Thus, the present invention does not rely solely on the use of optical properties to decode the arrays. However, as will be appreciated by those in the art, it is possible in some embodiments to utilize optical signatures as an additional coding method, in conjunction with the present system. Thus, for example, as is more fully outlined below, the size of the array may be effectively increased while using a single set of decoding probes in several ways, one of which is the use of optical signatures one some beads. Thus, for example, using one "set" of decoding probes, the use of two populations of beads, one with an optical signature and one without, allows the effective doubling of the array size. The use of multiple optical signatures similarly increases the possible size of the array.

In addition, the use of different concentrations or densities of IPs allows a "reuse" of sorts. If, for example, the bead comprising a first agent has a 1× concentration of IP, and a second bead comprising a second agent has a 10× concentration of IP, using saturating concentrations of the corresponding labelled DP allows the user to distinguish between the two beads.

Once the microspheres comprising the candidate agents and the identifier probes (or, in the case where the candidate agents are nucleic acids, just the candidate agents) are generated, they are added to the substrate to form an array. In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads removed.

It should be noted that not all sites of an array may comprise a bead; that is, there may be some sites on the substrate surface which are empty. In addition, there may be some sites that contain more than one bead, although this is not preferred.

In some embodiments, for example when chemical attachment is done, it is possible to attach the beads in a non-random or ordered way. For example, using photoactivatible attachment linkers or photoactivatible adhesives or masks, selected sites on the array may be sequentially rendered suitable for attachment, such that defined populations of beads are laid down.

Generally, decoding the array proceeds via a set of combinatorial decoding probes. There are two general types of decoding sets: those that rely on universal bases and those that do not.

Accordingly, in a preferred embodiment, the present invention provides decoding compositions comprising a plurality of nucleic acids. In a preferred embodiment, each decoding nucleic acid of the decoding composition is the same length, that is, contains the same number of bases. This is preferable because it generally simplifies the hybridization conditions required to discriminate the perfect and imperfect complementarity required in the intention. Alternatively, the plurality of nucleic acids comprises subsets each with the same number of nucleic acids, but each subset comprising a discrete number of bases.

By "plurality" in this context is meant at least two sets of nucleic acids, although in a more preferred embodiment "plurality" indicates at least 4 sets, that is, the plurality should preferably comprise four subsets of nucleic acids, each subset comprising a unique nucleotide at the decoding position of the variable position as described below. In an additional preferred embodiment "plurality" indicates at least 8 sets of nucleic acids.

In this embodiment, each decoding nucleic acid comprises an invariant or priming sequence. As outlined herein, this priming sequence is substantially complementary to the primer sequence of the identifier probe and thus will hybridize to it. By "invariant" or "priming" sequence herein is meant that portion of the decoding probe that is substantially complementary to the primer sequence of the identifier probe on the bead. In a preferred embodiment, all priming sequences are identical.

In this embodiment, each decoding nucleic acid comprises a variable sequence. By "variable" sequence herein is meant that portion of the decoding probe that comprises at least one position that comprises different nucleotides.

The variable sequence comprises at least one, and generally a plurality (e.g. at least two) of decoding nucleotide positions (sometimes referred to herein as "detection positions"). By "decoding nucleotide position" or "detection position" herein is meant the nucleotide position under interrogation; that is, it will basepair with the corresponding coding position on the identifier nucleic acid on the bead. As will be appreciated by those in the art, generally a variable sequence comprises a string of decoding positions, with each decoding step elucidating the base at one decoding position.

In one embodiment, the variable region comprises one position. That is, the set of decoder probes comprises the invariant region and one variable position that comprises each nucleotide used in the synthesis of the nucleic acid. Generally, this includes each of the frequently used nucleotides A, T, G, C or U. In this embodiment, the variable region is also the detection position.

In an alternative embodiment, the detection position comprises a random distribution of only that number of nucleotides desired to be included in the decoding segment of the nucleic acid. That is, when it is not necessary to have the probe complexity that results from the random distribution of 4 nucleotides, it may be desirable to have probes that have a random distribution of only 2 or 3 nucleotides at each detection position.

In another embodiment, the variable region comprises more than one nucleotide. That is, the variable region comprises at least one nucleotide position in addition to the detection position. Accordingly, by "spacer nucleotides" or "spacer positions" is meant the nucleotides in the variable region other than the detection position. In this embodiment, at each spacer nucleotide position all possible nucleotides are represented in at least one nucleic acid of the set. Alternatively, as outlined herein, universal bases are used. That is, like the detection nucleotide, spacer positions also comprise combinatorial nucleotides, however, they are not labeled. This allows for discrimination of the detection nucleotide.

In a preferred embodiment, the library of decoding probes comprises all possible variable sequences for a given length. That is, at each position of the variable sequence, at least one nucleic of the library comprises each nucleotide utilized in the synthesis of the nucleic acid. Thus, the variable sequences comprise combinatorial nucleotides or a random distribution of all possible combinations of nucleotides used in the synthesis of the variable sequence.

In a preferred embodiment, each decoding probe comprises a label. In a preferred embodiment, the nucleotide decoding position comprises the label. That is, the same position in each nucleic acid of a set comprises a label. By "label" or "labeled" herein is meant that a compound has at least one element, isotope or chemical compound attached to enable the detection of the compound. Preferably, each label is specific to a particular nucleotide. That is, A is labeled with a discrete label; T is labeled with a discrete label etc. In general, labels fall into three classes: a) isotopic labels, which may be radioactive or heavy isotopes; b) magnetic, electrical, thermal; and c) colored or luminescent dyes; although labels include enzymes and particles such as magnetic particles as well. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, and others described in the 6th Edition of the Molecular Probes Handbook by Richard P. Haugland, hereby expressly incorporated by reference. Additional labels include nanocrystals or Q-dots as described in U.S. Ser. No. 09/315,584, hereby expressly incorporated by reference.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels find particular use in systems requiring separation of labeled and unlabeled probes, such as SBE, OLA, invasive cleavage reactions, etc; in addition, these techniques may be used with many of the other techniques described herein. Secondary labels include, but are not limited to, one of a binding partner pair; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detection label (for example, attached to the NTP and therefore to the extended primer) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ $M^{-1}$, with less than about $10^{-5}$ to 10 $M^{-1}$ being preferred and less than about $10^{-7}$-$10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference).

However, in some embodiments, each nucleotide of the detection position is labeled with the same label, for example when four reactions or detection steps are performed as outlined herein, or when four arrays are analyzed. In a preferred embodiment, as is more fully outlined herein, the label is a fluorophore. In a preferred embodiment, the label is attached to the base of the nucleotide.

In an alternative embodiment, the decoding compositions comprise a plurality or library of nucleic acids comprising variable sequences comprising a plurality of nucleotide decoding positions. In a preferred embodiment, by "library" herein is meant at least two sets of nucleic acids, although in a more preferred embodiment "library" indicates at least 4 sets, while in most preferred embodiment "library" indicates at least 8 sets of nucleic acids.

In a preferred embodiment, when the variable sequence comprises a plurality of nucleotide decoding positions, at least one of the plurality comprises at least one universal base as described herein in the variable sequence. When universal bases are used, it should be understood that other nucleotides do not occupy this position.

In some embodiments, each nucleic acid of the plurality or library comprises a plurality of universal bases. In some embodiments universal bases occupy some, but not all of the spacer positions. That is, the variable region may comprise any combination of positions comprising universal bases and positions comprising random nucleotides. In a preferred embodiment, universal bases and random nucleotides comprise alternate positions of the spacer positions. For example, X-N-X-N . . . , where X indicates a universal base, and N represents either A, T, G, C or U.

In one embodiment, universal bases are used in some subset of the positions. This allows the complexity of the probe set to be reduced while retaining specificity. For example, universal bases could be incorporated at every other position, every two positions, etc. In some embodiments it may be desirable to intersperce sections of universal bases with "tack down" points of non-universal bases.

In an alternative embodiment, universal bases are used in every position that is not part of the priming sequence nor is the decoding position; this will result in only four decoding probes used.

In a preferred embodiment, only one type of universal base is used in all the decoding probes. However, this may not be desirable when the universal base has some residual sequence bias. Thus, in a preferred embodiment, mixtures of universal bases are used. In general, this may be done in several ways. In a preferred embodiment, two (or more) different universal bases are alternated within the probes (ABABABAB, etc.). Alternatively, the universal bases may be mixed at each position ((A/B)(A/B)(A/B)(A/B)(A/B)(A/B), etc.). The latter results in a more complex probe set, but the use of two universal bases requires fewer decoding probes than if all four bases are used.

In a preferred embodiment the detection position comprises the terminal nucleotide position of the nucleic acid sequence of the set. As an example, the nucleic acid comprises in a 5' to 3' orientation (although the reverse orientation i.e. 3' to 5', also would work):

5'-constant region-variable region (including spacer positions)-detection position*-3', where * indicates a label.

In an alternative embodiment, the detection position is not the terminal position, but rather there are additional spacer positions 3' to the detection position. As an example, the nucleic acid comprises in a 5' to 3 orientation:

5'-constant region-spacer nucleotide(s)-detection position*-spacer nucleotides-3', where * indicates a label.

Generally, the decoder probes comprise from 4 basepairs in length to about 1000, with from about 6 to about 100 being preferred, and from about 8 to about 40 being particularly preferred.

Accordingly, the invention provides kits comprising a plurality of sets of nucleic acids as described above. In a preferred embodiment the kit comprises sets of nucleic acids wherein the variable region of each set comprises a different length. That is, one set comprises a variable region comprising one nucleotide, another set comprises a variable region comprising 2 nucleotides, etc. Theoretically, there is no upper limit to the length of the variable region; accordingly, there is no theoretical upper limit to the size of the set. However, from a practical standpoint, the variable region is preferably from 1 to 1000 nucleotides in length, with from 1 to 100 nucleotides in length preferred, and from 1 to 30 being particularly preferred.

In a preferred embodiment, the kit comprises sets of nucleic acids comprising all successive lengths of nucleic acids up to the maximal length desired. That is, if it is desired to have a maximal length of 10 nucleotides in the variable region, the kit comprises a set with a variable region of 1 nucleotide, a set with a variable region of 2, a set with a variable region of 3, a set with a variable region of 4, a set with a variable region of 5, a set with a variable region of 6, a set with a variable region of 7, a set with a variable region of 8, a set with a variable region of 9, and a set with a variable region of 10 nucleotides.

In an alternative embodiment, the kits comprise sets of nucleic acids with only a subset of successive lengths represented in the kit. That is, it may not be necessary for a particular kit to comprise the degree of complexity of nucleic acids that would result from having all possible combinations of nucleotides at each position of the variable region. This is particularly true as the variable region increases in length. Accordingly, the kits are designed such that only a subset of probe lengths are included in the kit.

In a preferred embodiment, the detection position of each set is the terminal nucleotide of the nucleic acid. Preferably, the detection position comprises a label, as described above.

In a particularly preferred embodiment, the kit comprises sets of nucleic acids, wherein the length of the variable region is constant. However, in this embodiment, the position of the detection position is distinct for each set. That is, in one set the detection position is at the first position of the variable region; in another set, the detection position is at the second position, etc.

In one embodiment, the kit comprises sets, where the detection position is located at all possible positions of the variable region in a particular set of the kit. That is, for example, as described above, when the variable region comprises 10 nucleotides, the kit comprises a set with the detection at the first position, a set with the detection position at the second position etc. As described above, the nucleotide at the detection position is labeled.

One potential drawback to this approach is that large numbers of decoding probes must be used to decode longer probes. Thus, to decode 6 positions requires 4096 probes, 7 positions requires 16384 probes, etc. However one significant advantage of the present invention is that decoding probes can be made using combinatorial split and mix synthesis. Thus, although there is still a requirement for large numbers of probes, the probe synthesis is no longer a cumbersome step because of the power of the combinatorial approach to synthesis. An example is illustrative.

In the first step, a supply of the BDEFHIJ sequence is prepared. BDEFHIJ is complementary to the primer sequence SUVWXYZ (described above). First, four solutions are used to add A, C, G, and T to the complementary sequence to make decoding sequences 1a-d. Most of solutions 1a-d are combined. Next, the four solutions are labeled such that A is coupled to $F_1$, C is coupled to $F_2$ G is coupled to $F_3$ and T is coupled to $F_4$. These labeled sequences are then pooled to form decoding solution 1.

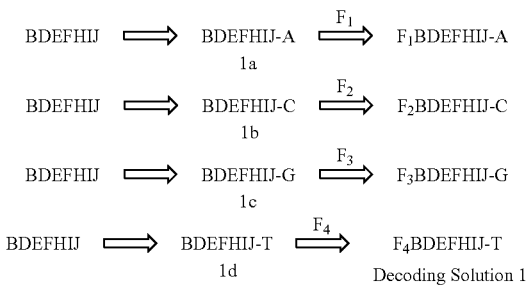

The combined, but unlabeled, 1a-d pooled solution is then divided into four portions and used iteratively in split and mix to prepare all possible sequences up to n-mers.

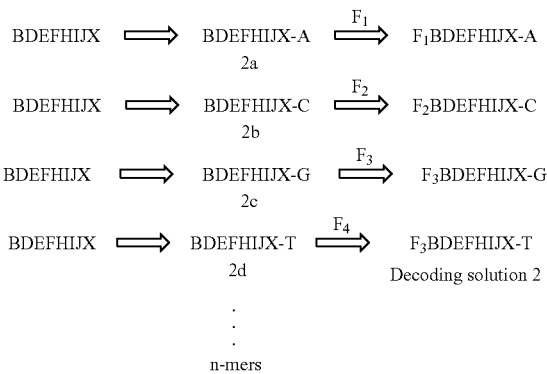

In each case, as the pool is extended by one base, one additional solution is created containing all possible sequences of that length with the four terminal nucleotides encoded by one of the different fluorecent labels.

Accordingly, for decoding to proceed, the decoding probes of the invention are added to the array. The detection of the label indicates the nucleotide present at the detection position of the decoder probe, or indicates the complement of the position being interrogated in the decoder portion of the identifier probe.

In a preferred embodiment, the decoding probes of the invention are used in sets, and sequentially decode one base at a time, starting with the base adjacent to the primer sequence. Thus, the detection nucleotide is positioned such that it interrogates a nucleotide of the decoding sequence of the identifier probe. The first detection position is directly adjacent to the primer sequence; the second detection position is adjacent to the first; the third is adjacent to the second; etc. Once the nucleotide of the first detection position has been elucidated, the first set of decoding probes are removed, and, if additional sequence information is required, a second set is added. As described above, in a preferred embodiment, the detection position is the terminal position of the probe. In this embodiment, each set of probes comprises probes of successively increasingly length because of the addition of a new detection position to the terminus of the probe. When decoding using decoding probes wherein the detection position is the terminal position of the probe, it may be necessary to use higher stringency conditions than, for example, when decoding using probes wherein the detection position is an internal nucleotide. In a preferred embodiment, formamide is included to increase stringency.

In an alternative embodiment, the detection position is not necessarily the terminal position, but rather an internal position of the variable portion of the decoder probe. In this embodiment, the probes can be the same length and sets differ by the position of the detection nucleotide.

For each detection position, a set of decoding probes is used. By "set" herein is meant a plurality of probes, each with a different sequence, that is used to elucidate the identity of the detection position and as a result identify the sequence of the decoding sequence of the identifier probe. Within each set, there are preferably at least four subsets of probes, each subset comprising a different nucleotide at the detection position, i.e. a different detection nucleotide. As outlined herein, there may be more than four subsets of probes, particularly when no universal bases are used and it is the second, third, etc. detection position that is being elucidated.

For decoding to proceed, a first set of combinatorial decoding probes is added to the array. Each decoding probe comprises a priming sequence complementary to the primer sequence of the identifier probes. In a preferred embodiment, the priming sequence is perfectly complementary to the primer sequence, although in some embodiments, some mismatches are acceptable and substantial complementarity is acceptable.

An example is illustrative of the system. An identifier probe comprises the sequence ATCGATCGTACTAC (SEQ ID NO: 33) with the primer being shown in italics and the first decoding position in bold. A first set of decoder probes is added, comprising TAGCTAGCA, TAGCTAGCT, TAGCTAGCC and TAGCTAGCG, with the priming sequence shown in italics and the decoding nucleotide underlined. Each of the decoding nucleotides comprises a detectable label distinguishable from the others, preferably a fluorophore as outlined herein. The first decoder probe, TAGCTAGCA, will hybridize more efficiently, and the signal from the A label will be more intense than the signal from the other three decoding probes. Thus, the first base of the identifier probe can be identified as a T.

In a preferred embodiment, a second set of decoding probes is added. In this second round, the position of the second decoding position is shown in bold, ATCGATCGTACTAC (SEQ ID NO: 33). A preferred embodiment utilizes 16 decoding probes: 4 probes having the sequence TAGCTAGCXA (SEQ ID NO: 34), where X is either A, T, C or G; 4 probes having the sequence TAGCTAGCXT (SEQ ID NO: 35), where X is either A, T, C or G; 4 probes having the sequence TAGCTAGCXC (SEQ ID NO: 36), where X is either A, T, C or G; and 4 probes having the sequence TAGCTAGCXG (SEQ ID NO: 37), where X is either A, T, C or G. In a sense, the first decoding position then becomes part of the primer/priming sequence. In this case, the TAGCTAGCAT (SEQ ID NO: 38) probe will hybridize the most efficiently. This can be repeated for additional cycles.

The decoding probes are added under hybridization conditions that allow differentiation between the subset that is exactly complementary to the decoding sequence and those that are not.

In general, the first set of decoding probes is added, allowed to hybridize for some period of time, and the excess (non-hybridized) probes are washed off. Detection of the fluorophore then proceeds as outlined below. Following detection of the first set of probes, the probes are removed, for example by heating, and a second set of decoder probes is added.

In this way, by sequentially adding sets of decoding probes, the sequence of the decoding sequence of the identifier probe is elucidated, thus allowing a correlation of the identifier probe to a location on the array, and, if applicable, the identification of the bound candidate agent as well.

When combinatorially prepared probes are used, all nucleotides appear at each position of the decoding segment of the probe. As such, in each set of decoder probes, there is a perfect complement for each identifier probe, however, only the terminal base is decoded at each step. The process of dehybridization followed by exposure to subsequent decoder probes continues until the entire array has been positionally decoded. In a sense, the process walks along the probes and sequences them one base at a time. In this manner, over a million sequences in the array can be decoded upon exposure to only 10 decoder probe sets ($4^{10}$), as exemplified in the following table (Table 2).

TABLE 2

Codes scale exponentially while decoding steps increase linearly. E.g. four colors and five sequential hybridizations can identify 1,024 probes.

| Number of fluors | Sequential steps | Number of codes | Expanded |
|---|---|---|---|
| 4 | 5 | $4^5$ | =1,024 |
| 4 | 10 | $4^{10}$ | =1,048,576 |
| n | m | $n^m$ | |

In an alternative embodiment, when each nucleotide of the detection position is labeled with the same label, decoding may still proceed. In this embodiment, after each step of the split and mix synthesis, as described above, aliquots of each solution are set aside as four separate decoding solutions. The remainder of the solutions are pooled and split and mix synthesis proceeds. Decoding is accomplished by exposing the array to each decoding probe sequentially and analyzing the label. Although decoding in this manner necessitates additional steps, the user only needs to label probes with a single label. In addition, label detection is facilitated when the user does not have the equipment to analyze multiple different signals. An example is illustrative.

Again, the primer sequence BDEFGHIJ is synthesized. However, in contrast to the synthesis above that utilized a different fluor for each additional nucleotide, in this embodiment, the same fluor is used at each step of synthesis, although different nucleotides are added the primer sequence.

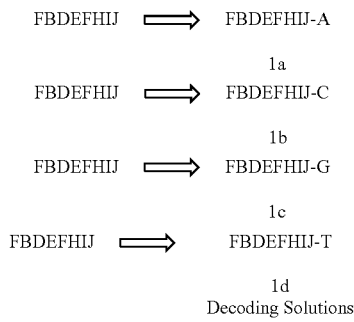

Decoding Solutions

Aliquots of solutions 1a-d are kept as four separate decoding solutions. Most of solutions 1a-d are pooled, separated into four reaction vessels and treated with the four nucleotides A, C, G, T. The process continues until all decoding solutions are made. This approach differs from the first one in that the same dye is used to label all sequences. Decoding is accomplished by exposing the array to each of the decoding solutions sequentially. For example decoding solution 1a will decode for the beads with A at position $X_1$. After exposure to decoding solution 1a, the array is rinsed and exposed to decoding solution 2a. The imaging system simply subtracts the fluorescent image after solution 1b from the solution 1a image and the difference highlights all the sequences containing C at position $X_1$. The process is repeated with solutions 1c and 1d, The array is then dehybridized to allow the next four solutions 2a-d to decode position $X_2$. The process is repeated until all the positions are decoded. The differences with this approach are only one dye is employed and the decoding at each position is accomplished by sequential exposure to the individual decoding solutions.

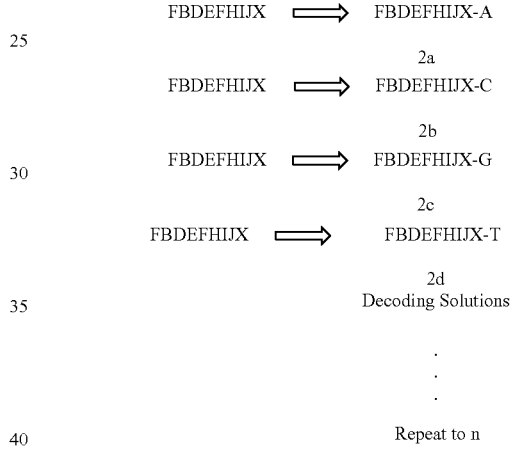

Decoding Solutions

Repeat to n

In an alternative embodiment, decoder probes that make use of internal (as opposed to terminal) detection nucleotides are used to decode the array.

The success of the decoding approaches described above depends on the fidelity of hybridization. The schemes above rely on the ability to differentiate sequences at the terminal base pair.

A particular preferred embodiment includes an alternative approach that can be employed in which internal bases are used to decode. In this approach, internal sequence positions are decoded with essentially the same scheme employed above. An example is illustrative. X represents all possible bases at the designated positions. In this manner, stringency requirements can be relaxed due to the lower propensity for internal mismatches to hybridize.

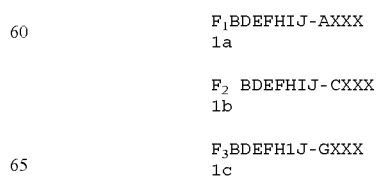

```
-continued
F₄  BDEFHIJ-TXXX
1d
Decoding Solution 1
```

One potential difficulty with this approach is the extraordinary complexity of the individual decoding solutions. For example, if it is required to decode a 10mer, the decoding solution will contain over one million sequences. The complexity of this solution may cause hybridization difficulties due to hybrid stability and/or local structure. An alternative decoding approach would employ universal bases in which all positions except for the decoding position are substituted with bases that can hybridize to all nucleotides. In this approach, the synthesis of the decoding solutions would be similar except that X=universal base, greatly simplifying the complexity of the decoding solution.

In addition, since from a practical standpoint the size of the array will depend on the number of decoding probes which can be easily handled, it is possible to "reuse" a set of decoding probes to allow for a greater number of test sites. This may be done in several ways; for example, by using some subpopulations of beads that comprise optical signatures. Similarly, the use of a positional coding scheme within an array; different sub-bundles may reuse the set of DPs. Similarly, one embodiment utilizes bead size as a coding modality, thus allowing the reuse of the set of unique DPs for each bead size. Alternatively, sequential partial loading of arrays with beads can also allow the reuse of DPs. Furthermore, "code sharing" can occur as well.

In a preferred embodiment, the DPs may be reused by having some subpopulations of beads comprise optical signatures. In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique optical signatures may be generated. This may be done by covalently attaching the dyes to the surface of the beads, or alternatively, by entrapping the dye within the bead. The dyes may be chromophores or phosphors but are preferably fluorescent dyes, which due to their strong signals provide a good signal-to-noise ratio for decoding. Suitable dyes for use in the invention include those listed above as useful as labels.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the pores of the beads.

Additionally, encoding in the ratios of the two or more dyes, rather than single dye concentrations, is preferred since it provides insensitivity to the intensity of light used to interrogate the reporter dye's signature and detector sensitivity.

In a preferred embodiment, a spatial or positional coding system is done. In this embodiment, there are sub-bundles or subarrays (i.e. portions of the total array) that are utilized. By analogy with the telephone system, each subarray is an "area code", that can have the same tags (i.e. telephone numbers) of other subarrays, that are separated by virtue of the location of the subarray. Thus, for example, the same unique tags can be reused from bundle to bundle. Thus, the use of 50 unique tags in combination with 100 different subarrays can form an array of 5000 different bioactive agents. In this embodiment, it becomes important to be able to identify one bundle from another; in general, this is done either manually or through the use of marker beads, i.e. beads containing unique tags for each subarray.

In alternative embodiments, additional encoding parameters can be added, such as microsphere size. For example, the use of different size beads may also allow the reuse of sets of DPs; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different bioactive agent (or the subpopulations each comprise a different bioactive agent), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each bioactive agent is determined, generally through the use of DPs. The second sublibrary is then added, and the location of each bioactive agent is again determined. The signal in this case will comprise the signal from the "first" DP and the "second" DP; by comparing the two matrices the location of each bead in each sublibrary can be determined. Similarly, adding the third, fourth, etc. sublibraries sequentially will allow the array to be filled.

In a preferred embodiment, codes can be "shared" in several ways. In a first embodiment, a single code (i.e., IP/DP pair) can be assigned to two or more agents if the target analytes different sufficiently in their binding strengths. For example, two nucleic acid probes used in an mRNA quantitation assay can share the same code if the ranges of their hybridization signal intensities do not overlap. This can occur, for example, when one of the target sequences is always present at a much higher concentration than the other. Alternatively, the two target sequences might always be present at a similar concentration, but differ in hybridization efficiency.

Alternatively, a single code can be assigned to multiple agents if the agents are functionally equivalent. For example, if a set of oligonucleotide probes are designed with the common purpose of detecting the presence of a particular gene, then the probes are functionally equivalent, even though they may differ in sequence. Similarly, if classes of analytes are desired, all probes for different members of a class such as kinases or G-protein coupled receptors could share a code. Similarly, an array of this type could be used to detect homologs of known genes. In this embodiment, each gene is represented by a heterologous set of probes, hybridizing to different regions of the gene (and therefore differing in sequence). The set of probes share a common code. If a homolog is present, it might hybridize to some but not all of the probes. The level of homology might be indicated by the fraction of probes hybridizing, as well as the average hybridization intensity. Similarly, multiple antibodies to the same protein could all share the same code. Other aspects of coding and decoding are described in U.S. Ser. Nos. 60/090,473, filed Jun. 24, 1998, 09/189,543, filed Nov. 10, 1998, 09/344,526, filed Jun. 24, 1999, and 60/172,106, filed Dec. 23, 1999, all of which are expressly incorporated herein by reference.

In addition, while preferred embodiments utilize the complete decoding of every identifier probe on the array, it is also possible to decode less than the complete array. For example, in a preferred embodiment, a selective decoding system is used. In this case, only those microspheres exhibiting a change in the optical signal as a result of the binding of a target analyte are decoded. This is commonly done when the number of "hits", i.e. the number of sites to decode, is generally low. That is, the array is first scanned under experimental conditions in the absence of the target analytes. The sample containing the target analytes is added, and only those locations exhibiting a change in the optical signal are decoded. For example, the beads at either the positive or negative signal locations may be either selectively tagged or released from the array (for example through the use of photo cleavable linkers), and subsequently sorted or enriched in a FACS. That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags mass spectral tags.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead contains a fluorescent dye. After the assay and the identification of the "positives" or "active beads", light is shone down either only the positive fibers or only the negative fibers, generally in the presence of a light-activated reagent (typically dissolved oxygen). In the former case, all the active beads are photobleached. Thus, upon non-selective release of all the beads with subsequent sorting, for example using a fluorescence activated cell sorter (FACS) machine, the non-fluorescent active beads can be sorted from the fluorescent negative beads. Alternatively, when light is shone down the negative fibers, all the negatives are non-fluorescent and the positives are fluorescent, and sorting can proceed. The characterization of the attached bioactive agent may be done directly, for example using mass spectroscopy.

Alternatively, rather than having each bead contain a fluorescent dye, each bead comprises a non-fluorescent precursor to a fluorescent dye. For example, using photocleavable protecting groups, such as certain ortho-nitrobenzyl groups, on a fluorescent molecule, photoactivation of the fluorochrome can be done. After the assay, light is shone down again either the "positive" or the "negative" fibers, to distinguish these populations. The illuminated precursors are then chemically converted to a fluorescent dye. All the beads are then released from the array, with sorting, to form populations of fluorescent and non-fluorescent beads (either the positives and the negatives or vice versa).

In an alternate preferred embodiment, the sites of attachment of the beads (for example the wells) include a photopolymerizable reagent, or the photopolymerizable agent is added to the assembled array. After the test assay is run, light is shone down again either the "positive" or the "negative" fibers, to distinguish these populations. As a result of the irradiation, either all the positives or all the negatives are polymerized and trapped or bound to the sites, while the other population of beads can be released from the array.

Accordingly, the identification of the location of the individual beads (or subpopulations of beads) is accomplished using one or more decoding steps comprising a binding between the labeled DP and the IP. After decoding, the DPs can be removed and the array can be used; however, in some circumstances, for example when the DP binds to an IP and not to the bioactive agent, the removal of the DP is not required (although it may be desirable in some circumstances). In addition, as outlined herein, decoding may be done either before the array is used in an assay, during the assay, or after the assay.

Once made, the compositions of the invention find use in a number of applications. In a preferred embodiment, the compositions are used to probe a sample solution for the presence or absence of a target analyte, including the quantification of the amount of target analyte present. By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (i.e., drug candidate) is sought.

Suitable analytes include organic and inorganic molecules, including biomolecules. When detection of a target analyte is performed, suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are nucleic acids and proteins.

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins.

In a preferred embodiment, the target analyte is a nucleic acid. These assays find use in a wide variety of applications. Additional applications include those as described in U.S. Ser. Nos. 60/130,089, filed Apr. 20, 1999, 60/160,027, filed Oct. 22, 1999, 09/513,362, filed Feb. 25, 2000, 60/135,051, filed May 20, 1999, 60/161,148, filed Oct. 22, 1999, 09/517,945, filed Mar. 3, 2000, 60/135,053, filed May 20, 1999, 09/425,633, filed Oct. 22, 1999, 09/535,854, filed Mar. 27, 2000, 09/533,993, filed Apr. 20, 2000 and 09/556,463, filed Apr. 21, 2000, all of which are expressly incorporated herein by reference.

In a preferred embodiment, the probes are used in genetic diagnosis. For example, probes can be made using the techniques disclosed herein to detect target sequences such as the gene for nonpolyposis colon cancer, the BRCA1 and BRCA2 breast cancer genes, p53, which is a gene associated with a variety of cancers, the Apo E4 gene that indicates a greater risk of Alzheimer's disease, allowing for easy presymptornatic screening of patients, mutations in the cystic fibrosis gene, cytochrome p450s or any of the others well known in the art.

In an additional embodiment, viral and bacterial detection is performed using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, chlamydia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization; see U.S. Pat. Nos. 5,695,940, 5,202,231 and 5,525,464, all of which are incorporated by reference.

The present invention also finds use as a methodology for the detection of mutations or mismatches in target nucleic acid sequences. For example, recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs). which occur at an average frequency of more than 1 per kilobase in human genomic DNA. Some SNPs. particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Cordor et al., Science 261 (1993)). Multiplex PCR amplification of SNP loci with subsequent hybridization to oligonucleotide arrays has been shown to be an accurate and reliable method of simultaneously genotyping at least hundreds of SNPs; see Wang et al, Science, 280: 1077 (1998); see also Schafer et al., Nature Biotechnology 16:33-39 (1998). The compositions of the present invention may easily be substituted for the arrays of the prior art.

In a preferred embodiment, the compositions of the invention are used to screen bioactive agents to find an agent that will bind, and preferably modify the function of, a target molecule. As above, a wide variety of different assay formats may be run, as will be appreciated by those in the art. Generally, the target analyte for which a binding partner is desired is labeled; binding of the target analyte by the bioactive agent results in the recruitment of the label to the bead, with subsequent detection.

In a preferred embodiment, the binding of the bioactive agent and the target analyte is specific; that is, the bioactive agent specifically binds to the target analyte. By "specifically bind" herein is meant that the agent binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding, although in some embodiments, wash steps are not desired; i.e. for detecting low affinity binding partners. In some embodiments, for example in the detection of certain biomolecules, the dissociation constants of the analyte to the binding ligand will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

Generally, a sample containing a target analyte (whether for detection of the target analyte or screening for binding partners of the target analyte) is added to the array, under conditions suitable for binding of the target analyte to at least one of the bioactive agents, i.e. generally physiological conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optical interrogatable event.

In a preferred embodiment, the change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorochromes, for example during PCR amplification as is known in the art. Alternatively, upon binding of the target sequences, a hybridization indicator may be used as the label. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, only in the presence of target hybridization will the label light up. Thus, upon binding of the target analyte to a bioactive agent, there is a new optical signal generated at that site, which then may be detected.

Alternatively, in some cases, as discussed above, the target analyte such as an enzyme generates a species that is either directly or indirectly optical detectable.

Furthermore, in some embodiments, a change in the optical signature may be the basis of the optical signal. For example, the interaction of some chemical target analytes with some fluorescent dyes on the beads may alter the optical signature, thus generating a different optical signal.

As will be appreciated by those in the art, in some embodiments, the presence or absence of the target analyte may be performed using changes in other optical or non-optical signals, including, but not limited to, surface enhanced Raman spectroscopy, surface plasmon resonance, radioactivity, etc.

The assays may be run under a variety of experimental conditions, as will be appreciated by those in the art. A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

In a preferred embodiment, two-color competitive hybridization assays are run. These assays can be based on traditional sandwich assays. The beads contain a capture sequence located on one side (upstream or downstream) of the SNP, to capture the target sequence. Two SNP allele-specific probes, each labeled with a different fluorophor, are hybridized to the target sequence. The genotype can be obtained from a ratio of the two signals, with the correct sequence generally exhibiting better binding. This has an advantage in that the target sequence itself need not be labeled. In addition, since the probes are competing, this means that the conditions for binding need not be optimized. Under conditions where a mismatched probe would be stably bound, a matched probe can still displace it. Therefore the competitive assay can provide better discrimination under those conditions. Because many assays are carried out in parallel, conditions cannot be optimized for every probe simultaneously. Therefore, a competitive assay system can be used to help compensate for non-optimal conditions for mismatch discrimination.

In a preferred embodiment, dideoxynucleotide chain-termination sequencing is performed using the compositions of the invention. In this embodiment, a DNA polymerase is used to extend a primer using fluorescently labeled ddNTPs. The 3' end of the primer is located adjacent to the SNP site. In this way, the single base extension is complementary to the sequence at the SNP site. By using four different fluorophors, one for each base, the sequence of the SNP can be deduced by comparing the four base-specific signals. This may be done in several ways. In a first embodiment, the capture probe can be extended; in this approach, the probe must either be synthesized 5'-3' on the bead, or attached at the 5' end, to provide a free 3' end for polymerase extension. Alternatively, a sandwich type assay can be used; in this embodiment, the target is captured on the bead by a probe, then a primer is annealed and extended. Again, in the latter case, the target sequence need not be labeled. In addition, since sandwich assays require two specific interactions, this provides increased stringency which is particularly helpful for the analysis of complex samples.

In addition, when the target analyte and the DP both bind to the agent, it is also possible to detect non-labeled target analytes via competition of decoding.

In a preferred embodiment, the methods of the invention are useful in array quality control. Prior to this invention, no methods have been described that provide a positive test of the performance of every probe on every array. Decoding of the array not only provides this test, it also does so by making use of the data generated during the decoding process itself. Therefore, no additional experimental work is required. The invention requires only a set of data analysis algorithms that can be encoded in software.

The quality control procedure can identify a wide variety of systematic and random problems in an array. For example, random specks of dust or other contaminants might cause some sensors to give an incorrect signal—this can be detected during decoding. The omission of one or more agents from multiple arrays can also be detected. An advantage of this quality control procedure is that it can be implemented immediated prior to the assay itself, and is a true functional test of each individual sensor. Therefore any problems that might occur between array assembly and actual use can be detected. In applications where a very high level of confidence is required, and/or there is a significant chance of sensor failure during the experimental procedure, decoding and quality control can be conducted both before and after the actual sample analysis.

In a preferred embodiment, the arrays can be used to perform reagent quality control. In many instances, biological macromolecules are used as reagents and must be quality controlled. For example, large sets of oligonucleotide probes may be provided as reagents. It is typically difficult to perform quality control on large numbers of different biological macromolecules. The approach described here can be used to do this by treating the reagents (formulated as the DPs) as variable instead of the arrays.

In a preferred embodiment, the methods outlined herein are used in array calibration. For many applications, such as mRNA quantitation, it is desirable to have a signal that is a linear response to the concentration of the target analyte, or, alternatively, if non-linear, to determine a relationship between concentration and signal, so that the concentration of the target analyte can be estimated. Accordingly, the present invention provides methods of creating calibration curves in parallel for multiple beads in an array. The calibration curves can be created under conditions that simulate the complexity of the sample to be analyzed. Each curve can be constructed independently of the others (e.g. for a different range of concentrations), but at the same time as all the other curves for the array. Thus, in this embodiment, the sequential decoding scheme is implemented with different concentrations being used as the code "labels", rather than different fluorophores. In this way, signal as a response to concentration can be measured for each bead. This calibration can be carried out just prior to array use, so that every probe on every array is individually calibrated as needed.

In a preferred embodiment, the methods of the invention can be used in assay development as well. Thus, for example, the methods allow the identification of good and bad probes; as is understood by those in the art, some probes do not function well because they do not hybridize well, or because they cross-hybridize with more than one sequence. These problems are easily detected during decoding. The ability to rapidly assess probe performance has the potential to greatly reduce the time and expense of assay development.

Similarly, in a preferred embodiment, the methods of the invention are useful in quantitation in assay development. A major challenge of many assays is the ability to detect differences in analyte concentrations between samples, the ability to quantitate these differences, and to measure absolute concentrations of analytes, all in the presence of a complex mixture of related analytes. An example of this problem is the quantitation of a specific mRNA in the presence of total cellular mRNA. One approach that has been developed as a basis of mRNA quantitation makes use of a multiple match and mismatch probe pairs (Lockhart et al., 1996, hereby incorporated by reference in its entirety). While this approach is simple, it requires relatively large numbers of probes. In this approach, a quantitative response to concentration is obtained by averaging the signals from a set of different probes to the gene or sequence of interest. This is necessary because only some probes respond quantitatively, and it is not possible to predict these probes with certainty. In the absence of prior knowledge, only the average response of an appropriately chosen collection of probes is quantitative. However, in the present invention, that can be applied generally to nucleic acid based assays as well as other assays. In essence, the approach is to identify the probes that respond quantitatively in a particular assay, rather than average them with other probes. This is done using the array calibration scheme outlined above, in which concentration-based codes are used. Advantages of this approach include: fewer probes are needed; the accuracy of the measurement is less dependent on the number of probes used; and that the response of the sensors is known with a high level of certainty, since each and every sequence can be tested in an efficient manner. It is important to note that probes that perform well are selected empirically, which avoids the difficulties and uncertainties of predicting probe performance, particularly in complex sequence mixtures. In contrast, in experiments described to date with ordered arrays, relatively small numbers of sequences are checked by performing quantitative spiking experiments, in which a known mRNA is added to a mixture.

All references cited herein are incorporated by reference in their entirety.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLE

Example 1

Identification of Sequence on Beads

The anchor consists of the following 8 mer:

3'-NH$_2$-G GAG CTG G-5'

The probe consists of the anchor +4 bases. The 4 base sequence used is AAAA. The probe is attached to the bead at the 3' end.

Targets

The target consists of the anchor's complement+4 bases: 5'-dye-C CTC GAC C+XXXX-3' (SEQ ID NO: 39). The dye is attached to the 5' end of the probe. The target mixture contains all 64 possible targets. Briefly: there are 4 solutions each containing 16 targets. Each of the $4_{(16)}$ target solutions has a different dye label and the base applied at, e.g., 9 is known. Once the 4 target solutions are mixed (named, e.g., Mx9), the total target number is 64.

Dyes

The 4 labels used in the experiment include: Cy5 (620/700), Cy3 (530/580), Fluorescein (495/530), Biotin (secondary reaction with F1-Streptavidin (495/530).

Experimental

Making Target Solutions in Buffer

The stock target solutions (16 targets) are diluted to a concentration of 10 µM in TE buffer pH 8.3 containing 0.1% SDS and 0.1M NaCl. Once the 4 target solutions are mixed, the final concentration of each probe is 156 nM.

a) The concentration of the targets with fluorescein was 3× the concentration of the other targets. The Fluorescein labeled target stock solutions were diluted to 30 µM before the 4 were mixed together.

Example of targets where position 9 is known:

| 16 targets with | Biotin label | 9A = anchor + AXXX | 10 µM |
| 16 targets with | Fluorescein label | 9T = anchor + TXXX | 30 µM |
| 16 targets with | Cy 5 label | 9C = anchor + CXXX | 10 µM |
| 16 targets with | Cy 3 label | 9G = anchor + GXXX | 10 µM | a) cont. Mix 20 µL of 9A, 9T, 9C and 9G.

Making Target Solutions in Formamide

The single base specificity was achieved in a 20-25% formamide solution.

The $4_{(16)}$ stock solutions (approx. 120 µM) were diluted with 25% formamide to 10 µM solutions.

| Imaging Parameters | |
|---|---|
| 40× objective | 1.5 magnifying lens No ND filter |
| Cy5 620/700 | 0.5 s acquisition time (divide final intensity by 2) |
| Cy3 530/589 | 0.5 s acquisition time (divide final intensity by 2) |
| Fluorescein (495/530) | 5 s acquisition time |

Assay with One Bead Type

The beads were placed in a fiber. The 4 base tail sequence was identified with 4 solutions (Mx9, Mx10, Mx11, Mx12). E.g., the fiber was placed in Mx9 for 5 minutes, rinsed in buffer, and images were acquired at the 3 wavelengths. The fiber was then placed in a 3 µg/ml F1-streptavidin solution. A second image was acquired at the 495/530 setting. To analyze the data for position 9, the average fluorescence intensity from (30) beads was acquired for each wavelength. The average background signal (3-5 blank wells) for each wavelength was subtracted from the average fluorescence intensity. (The F1-streptavidin intensity was the second (F1-streptavidin) 495 intensity minus the first fluorescein intensity.)

The designation of the base at each position was generated from the data acquired using 20% formamide. The label generating the highest fluorescence intensity was the perfect complement.

The process was repeated with probes labeled at positions 10, 11 and 12. Results are depicted in FIGS. 2-4.

What is claimed is:

1. A method of determining a nucleotide sequence of a polynucleotide, said method comprising the steps of:
   a) providing a substrate comprising a channel having a first subpopulation and a second subpopulation of captured nucleic acids distributed thereon, wherein captured nucleic acids of the first subpopulation and captured nucleic acids of the second subpopulation comprise an anchor sequence adjacent to a target sequence, the anchor sequence of the first subpopulation of captured nucleic acids having the same sequence as the anchor sequence of the second subpopulation of captured nucleic acids and the target sequence of the first subpopulation of captured nucleic acids being different from the target sequence of the second subpopulation of captured nucleic acids, wherein captured nucleic acids of the first subpopulation and captured nucleic acids of the second subpopulation are hybridized to a plurality of target probes comprising a variable region, said variable region comprising at least one detection nucleotide at a detection position, said detection nucleotide being able to basepair with a nucleotide of at least one of said different target sequences, wherein said plurality of target probes comprises different groups, and wherein target probes from different groups comprise a different detection nucleotide at the same detection position and a label that distinguishes the detection nucleotide;
   b) detecting the presence of said label; and
   c) associating the label with the identity of one or more nucleotides of the polynucleotide.

2. The method of claim 1, further comprising dehybridizing said target probes from said captured nucleic acids.

3. The method of claim 2, further comprising hybridizing a second set of target probes to said first and second subpopulations of captured nucleic acids and detecting the presence of a label in said target probes.

4. The method of claim 1, wherein said first and second subpopulations of captured nucleic acids are attached to beads that are distributed within the channel.

5. The method of claim 1, wherein said target sequence comprises a nucleic acid selected from the group consisting of: a fragment of a gene, a regulatory sequence, genomic DNA, cDNA, RNA, a fragment of genomic DNA, a fragment of mRNA, and a copy of a genomic DNA fragment.

6. The method of claim 1, wherein said plurality of target probes comprises at least four groups.

7. The method of claim 1, wherein said variable region comprises two detection nucleotides.

8. The method of claim 7, wherein the two detection nucleotides are internal nucleotides of the variable region.

9. The method of claim 7, wherein the first of the two detection nucleotides is at an end of the variable region.

10. The method of claim 9, wherein the second of the two detection nucleotides is immediately adjacent to the first detection nucleotide.

11. The method of claim 10, wherein said variable region further comprises a plurality of random nucleotides immediately adjacent to the second detection nucleotide.

12. The method of claim 1, wherein said variable region comprises a single detection nucleotide.

13. The method of claim 12, wherein the single detection nucleotide is an internal nucleotide of the variable region.

14. The method of claim 12, wherein the single detection nucleotide is at an end of the variable region.

15. The method of claim 14, wherein said variable region further comprises a plurality of random nucleotides immediately adjacent to the single detection nucleotide.

16. The method of claim 15, wherein said variable region further comprises a plurality of universal bases immediately adjacent to the plurality of random nucleotides.

17. The method of claim 1, wherein said label is located at one end of said variable region.

18. The method of claim 1, wherein said label is located at the detection position.

19. The method of claim 1, wherein the target sequence comprises no more than 1000 nucleotides.

20. The method of claim 1, wherein said plurality of target probes further comprises a priming sequence complementary to a portion of a primer sequence of said captured nucleic acids.

* * * * *

SEQUENCE LISTING

<160> NUMBER OF SEQ ID NOS: 39

<210> SEQ ID NO 1
<211> LENGTH: 12
<212> TYPE: DNA
<213> ORGANISM: Artificial Sequence
<220> FEATURE:
<223> OTHER INFORMATION: probe sequence

<400> SEQUENCE: 1
gcggtcccaa aa                                                          12

<210> SEQ ID NO 2
<211> LENGTH: 12
<212> TYPE: DNA
<213> ORGANISM: Artificial Sequence
<220> FEATURE:
<223> OTHER INFORMATION: decoding probes

<400> SEQUENCE: 2
gcggtcccga aa                                                          12

<210> SEQ ID NO 3
<211> LENGTH: 12
<212> TYPE: DNA
<213> ORGANISM: Artificial Sequence
<220> FEATURE:
<223> OTHER INFORMATION: decoding probes

<400> SEQUENCE: 3
gcggtcccac aa                                                          12

<210> SEQ ID NO 4
<211> LENGTH: 12
<212> TYPE: DNA
<213> ORGANISM: Artificial Sequence
<220> FEATURE:
<223> OTHER INFORMATION: decoding probes

<400> SEQUENCE: 4
gcggtccccg aa                                                          12

<210> SEQ ID NO 5
<211> LENGTH: 12
<212> TYPE: DNA
<213> ORGANISM: Artificial Sequence
<220> FEATURE:
<223> OTHER INFORMATION: decoding probes

<400> SEQUENCE: 5
gcggtcccca aa                                                          12

<210> SEQ ID NO 6
<211> LENGTH: 12
<212> TYPE: DNA
<213> ORGANISM: Artificial Sequence
<220> FEATURE:
<223> OTHER INFORMATION: decoding probes

<400> SEQUENCE: 6
gcggtcccta aa                                                          12

<210> SEQ ID NO 7
<211> LENGTH: 12
<212> TYPE: DNA

```
<213> ORGANISM: Artificial Sequence
<220> FEATURE:
<223> OTHER INFORMATION: decoding probes

<400> SEQUENCE: 7
gcggtcccag aa                                                              12

<210> SEQ ID NO 8
<211> LENGTH: 12
<212> TYPE: DNA
<213> ORGANISM: Artificial Sequence
<220> FEATURE:
<223> OTHER INFORMATION: probe sequence

<400> SEQUENCE: 8
gcggtcccat aa                                                              12

<210> SEQ ID NO 9
<211> LENGTH: 12
<212> TYPE: DNA
<213> ORGANISM: Artificial Sequence
<220> FEATURE:
<223> OTHER INFORMATION: probe sequence

<400> SEQUENCE: 9
gcggtcccgc aa                                                              12

<210> SEQ ID NO 10
<211> LENGTH: 12
<212> TYPE: DNA
<213> ORGANISM: Artificial Sequence
<220> FEATURE:
<223> OTHER INFORMATION: probe sequence

<400> SEQUENCE: 10
gcggtccctg aa                                                              12

<210> SEQ ID NO 11
<211> LENGTH: 12
<212> TYPE: DNA
<213> ORGANISM: Artificial Sequence
<220> FEATURE:
<223> OTHER INFORMATION: probe sequence

<400> SEQUENCE: 11
gcggtccccc aa                                                              12

<210> SEQ ID NO 12
<211> LENGTH: 12
<212> TYPE: DNA
<213> ORGANISM: Artificial Sequence
<220> FEATURE:
<223> OTHER INFORMATION: probe sequence

<400> SEQUENCE: 12
gcggtcccct aa                                                              12

<210> SEQ ID NO 13
<211> LENGTH: 12
<212> TYPE: DNA
<213> ORGANISM: Artificial Sequence
<220> FEATURE:
<223> OTHER INFORMATION: probe sequence

<400> SEQUENCE: 13
gcggtcccaa ga                                                              12
```

```
<210> SEQ ID NO 14
<211> LENGTH: 12
<212> TYPE: DNA
<213> ORGANISM: Artificial Sequence
<220> FEATURE:
<223> OTHER INFORMATION: probe sequence

<400> SEQUENCE: 14
gcggtcccaa ag                                                            12

<210> SEQ ID NO 15
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)...(11)
<223> OTHER INFORMATION: n= A, T, G, or C

<400> SEQUENCE: 15
cgccagggtn nt                                                            12

<210> SEQ ID NO 16
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)...(11)
<223> OTHER INFORMATION: n= A, T, G, or C

<400> SEQUENCE: 16
cgccagggcn nt                                                            12

<210> SEQ ID NO 17
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)...(11)
<223> OTHER INFORMATION: n= A, T, G, or C

<400> SEQUENCE: 17
cgccaggggn nt                                                            12

<210> SEQ ID NO 18
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)...(11)
<223> OTHER INFORMATION: n= A, T, G, or C

<400> SEQUENCE: 18
cgccagggan nt                                                            12

<210> SEQ ID NO 19
<211> LENGTH: 12
<212> TYPE: DNA
```

```
<213> ORGANISM: Artificial Sequence
<220> FEATURE:
<223> OTHER INFORMATION: synthetic
<220> FEATURE:
<221> NAME/KEY: misc_feature
<222> LOCATION: (9)...(9)
<223> OTHER INFORMATION: n= A, T, G, or C
<220> FEATURE:
<221> NAME/KEY: misc_feature
<222> LOCATION: (11)...(11)
<223> OTHER INFORMATION: n= A, T, G, or C

<400> SEQUENCE: 19
cgccagggnt nt                                                          12

<210> SEQ ID NO 20
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)...(9)
<223> OTHER INFORMATION: n= A, T, G, or C
<220> FEATURE:
<221> NAME/KEY: misc_feature
<222> LOCATION: (11)...(11)
<223> OTHER INFORMATION: n= A, T, G, or C

<400> SEQUENCE: 20
cgccagggnc nt                                                          12

<210> SEQ ID NO 21
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)...(9)
<223> OTHER INFORMATION: n= A, T, G or C
<220> FEATURE:
<221> NAME/KEY: misc_feature
<222> LOCATION: (11)...(11)
<223> OTHER INFORMATION: n= A, T, G, or C

<400> SEQUENCE: 21
cgccagggng nt                                                          12

<210> SEQ ID NO 22
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)...(9)
<223> OTHER INFORMATION: n= A, T, G, or C
<220> FEATURE:
<221> NAME/KEY: misc_feature
<222> LOCATION: (11)...(11)
<223> OTHER INFORMATION: n= A, T, G, or C

<400> SEQUENCE: 22
cgccagggna nt                                                          12

<210> SEQ ID NO 23
<211> LENGTH: 12
<212> TYPE: DNA
```

```
<213> ORGANISM: Artificial Sequence
<220> FEATURE:
<223> OTHER INFORMATION: synthetic

<400> SEQUENCE: 23
cgccagggtc tt                                                              12

<210> SEQ ID NO 24
<211> LENGTH: 12
<212> TYPE: DNA
<213> ORGANISM: Artificial Sequence
<220> FEATURE:
<223> OTHER INFORMATION: synthetic

<400> SEQUENCE: 24
cgccagggtg tt                                                              12

<210> SEQ ID NO 25
<211> LENGTH: 12
<212> TYPE: DNA
<213> ORGANISM: Artificial Sequence
<220> FEATURE:
<223> OTHER INFORMATION: synthetic

<400> SEQUENCE: 25
cgccagggta tt                                                              12

<210> SEQ ID NO 26
<211> LENGTH: 12
<212> TYPE: DNA
<213> ORGANISM: Artificial Sequence
<220> FEATURE:
<223> OTHER INFORMATION: synthetic

<400> SEQUENCE: 26
cgccagggtt ct                                                              12

<210> SEQ ID NO 27
<211> LENGTH: 12
<212> TYPE: DNA
<213> ORGANISM: Artificial Sequence
<220> FEATURE:
<223> OTHER INFORMATION: synthetic

<400> SEQUENCE: 27
cgccagggtt gt                                                              12

<210> SEQ ID NO 28
<211> LENGTH: 12
<212> TYPE: DNA
<213> ORGANISM: Artificial Sequence
<220> FEATURE:
<223> OTHER INFORMATION: synthetic

<400> SEQUENCE: 28
cgccagggtt at                                                              12

<210> SEQ ID NO 29
<211> LENGTH: 12
<212> TYPE: DNA
<213> ORGANISM: Artificial Sequence
<220> FEATURE:
<223> OTHER INFORMATION: synthetic

<400> SEQUENCE: 29
cgccagggtt tc                                                              12
```

```
<210> SEQ ID NO 30
<211> LENGTH: 12
<212> TYPE: DNA
<213> ORGANISM: Artificial Sequence
<220> FEATURE:
<223> OTHER INFORMATION: synthetic

<400> SEQUENCE: 30
cgccagggtt tg                                                         12

<210> SEQ ID NO 31
<211> LENGTH: 12
<212> TYPE: DNA
<213> ORGANISM: Artificial Sequence
<220> FEATURE:
<223> OTHER INFORMATION: synthetic

<400> SEQUENCE: 31
cgccagggtt ta                                                         12

<210> SEQ ID NO 32
<211> LENGTH: 12
<212> TYPE: DNA
<213> ORGANISM: Artificial Sequence
<220> FEATURE:
<223> OTHER INFORMATION: synthetic

<400> SEQUENCE: 32
gcggtcccct gg                                                         12

<210> SEQ ID NO 33
<211> LENGTH: 14
<212> TYPE: DNA
<213> ORGANISM: Artificial Sequence
<220> FEATURE:
<223> OTHER INFORMATION: indentifier probe

<400> SEQUENCE: 33
atcgatcgta ctac                                                       14

<210> SEQ ID NO 34
<211> LENGTH: 10
<212> TYPE: DNA
<213> ORGANISM: Artificial Sequence
<220> FEATURE:
<223> OTHER INFORMATION: decoding probes
<220> FEATURE:
<221> NAME/KEY: misc_feature
<222> LOCATION: (9)...(9)
<223> OTHER INFORMATION: n=A, T, G, or C

<400> SEQUENCE: 34 tagctagcna                                                            10

<210> SEQ ID NO 35
<211> LENGTH: 10
<212> TYPE: DNA
<213> ORGANISM: Artificial Sequence
<220> FEATURE:
<223> OTHER INFORMATION: decoding probes
<220> FEATURE:
<221> NAME/KEY: misc_feature
<222> LOCATION: (9)...(9)
<223> OTHER INFORMATION: n= A, G, T, or C

<400> SEQUENCE: 35 tagctagcnt                                                            10
```

```
<210> SEQ ID NO 36
<211> LENGTH: 10
<212> TYPE: DNA
<213> ORGANISM: Artificial Sequence
<220> FEATURE:
<223> OTHER INFORMATION: decoding probes
<220> FEATURE:
<221> NAME/KEY: misc_feature
<222> LOCATION: (9)...(9)
<223> OTHER INFORMATION: n= A, G, T, or C

<400> SEQUENCE: 36 tagctagcnc                                                          10

<210> SEQ ID NO 37
<211> LENGTH: 10
<212> TYPE: DNA
<213> ORGANISM: Artificial Sequence
<220> FEATURE:
<223> OTHER INFORMATION: decoding probes
<220> FEATURE:
<221> NAME/KEY: misc_feature
<222> LOCATION: (9)...(9)
<223> OTHER INFORMATION: n= A, G, T, or C

<400> SEQUENCE: 37 tagctagcng                                                          10

<210> SEQ ID NO 38
<211> LENGTH: 10
<212> TYPE: DNA
<213> ORGANISM: Artificial Sequence
<220> FEATURE:
<223> OTHER INFORMATION: probe sequence

<400> SEQUENCE: 38
tagctagcat                                                          10

<210> SEQ ID NO 39
<211> LENGTH: 12
<212> TYPE: DNA
<213> ORGANISM: Artificial Sequence
<220> FEATURE:
<223> OTHER INFORMATION: probe sequence
<220> FEATURE:
<221> NAME/KEY: misc_feature
<222> LOCATION: (9)...(12)
<223> OTHER INFORMATION: n= A, T, G, or C

<400> SEQUENCE: 39
cctcgaccnn nn                                                       12
```